(12) United States Patent
Tsubata et al.

(10) Patent No.: US 6,348,460 B1
(45) Date of Patent: Feb. 19, 2002

(54) 1,2,3-THIADIAZOLE DERIVATIVES, PLANT DISEASE CONTROLLER AND METHOD FOR USING THE SAME

(75) Inventors: Kenji Tsubata, Kawachinagano; Takashi Shimaoka, Sakai; Tateki Nishida, Tondabayashi; Kazuhiro Takagi, Osaka; Koji Baba, Kawachinagano; Sohkichi Tajima, Osaka, all of (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/437,240

(22) Filed: Nov. 10, 1999

Related U.S. Application Data

(63) Continuation of application No. PCT/JP98/02330, filed on May 27, 1998.

(30) Foreign Application Priority Data

May 28, 1997 (JP) .............................. 9-154418
Jun. 28, 1997 (JP) .............................. 9-187646

(51) Int. Cl.$^7$ ..................... A01N 43/86; C07D 265/20; C07D 279/08
(52) U.S. Cl. ............... 514/224.2; 514/224.5; 514/230.5; 514/224.8; 544/92; 544/93; 544/89; 544/50; 544/32
(58) Field of Search ............... 544/54, 92, 93, 544/89, 50, 32; 514/227.2, 230, 224.2, 230.5

(56) References Cited

U.S. PATENT DOCUMENTS

| | | | |
|---|---|---|---|
| 3,914,121 A | 10/1975 | Doyle, Jr. ...................... | 71/90 |
| 4,315,766 A | 2/1982 | Hamprecht et al. ............ | 544/92 |
| 4,523,942 A | 6/1985 | Hamprecht et al. ............ | 71/88 |

FOREIGN PATENT DOCUMENTS

| JP | WO 9629871 | * 10/1996 | |
|---|---|---|---|
| WO | 96/29871 | 10/1996 | |

* cited by examiner

*Primary Examiner*—John M. Ford
(74) *Attorney, Agent, or Firm*—Paul E. White, Jr.; Manelli Denison & Selter PLLC

(57) ABSTRACT

A 1,2,3-thiadiazole derivative represented by general formula (I):

(I)

[wherein R$^1$ is hydrogen atom, halogen atom, (C$_1$–C$_6$) alkyl, phenyl, etc., R$^2$ is the following group (A) or group (B):

(A)

(B)
—CON—S—(O)mR$^6$
  |
  R$^5$ (wherein R$^3$ is halogen atom, cyano, etc., R$^4$ is hydrogen atom, halogen atom, cyano, etc., X and Y, same or different, are oxygen atom or sulfur atom, n is 0–3, R$^5$ is hydrogen atom, (C$_1$–C$_{20}$) alkyl, etc., R$^6$ is (C$_1$–C$_{20}$) alkyl, (C$_2$–C$_{20}$) alkenyl, etc., and m is 0–2)]; a plant disease controller containing said compound as active ingredient; and a method for using said controller.

5 Claims, No Drawings

1,2,3-THIADIAZOLE DERIVATIVES, PLANT DISEASE CONTROLLER AND METHOD FOR USING THE SAME

This application is a Continuation of PCT Application No. PCT/JP98/02330, filed May 27, 1998 which designated the U.S.

TECHNICAL FIELD PERTINENT TO THE INVENTION

The present invention relates to 1,2,3-thiadiazole derivatives, plant disease controller containing said compounds as active ingredient thereof, and a method for using the same.

BACKGROUND ART

In JP-A-54-9272 are disclosed 1,2,3-thiadiazole-5-carboxylic acid derivatives, a method for producing said compounds, and compositions having herbicidal and plant growth regulating activities which contain said compounds. Further, in Canadian Patent No. 947297, JP-A-55-141476 and JP-A-56-108776, it is disclosed that benzoxazine derivatives are useful as herbicide.

The microorganisms and Eumycetes which are to be controlled with fungicides are characterized by rapidness of alteration of generations, and the problem of resistance to fungicides has long been discussed. Thus, it is desired to develop a novel fungicide having an excellent effect.

DISCLOSURE OF THE INVENTION

With the aim of developing a novel plant disease controller, the present inventors have continued elaborated studies to find that the 1,2,3-thiadiazole derivatives of the present invention represented by general formula (I) are useful as plant disease controller. Based on this finding, the present invention has been accomplished.

As typical compounds of the present invention, the 1,2,3-thiadiazole compounds represented by the following general formulas (I-a) and (I-b) can be referred to:

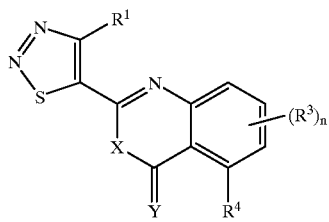

(I-a)

wherein $R^1$, $R^3$, $R^4$, n, X and Y are as defined later,

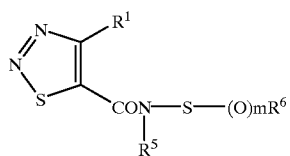

(I-b)

wherein $R^1$, $R^5$, $R^6$ and m are as defined later.

That is, the present invention relates to 1,2,3-thiadiazole derivatives represented by the following general formula (I), a plant disease controller containing said compounds as active ingredient thereof, and a method for using the same:

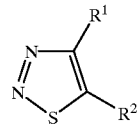

(I)

[wherein $R^1$ represents hydrogen atom, halogen atom, ($C_1$–$C_6$) alkyl group, halo ($C_1$–$C_6$) alkyl group, hydroxy ($C_1$–$C_6$) alkyl group, ($C_1$–$C_6$) alkoxy ($C_1$–$C_6$) alkyl group, ($C_3$–$C_6$) cycloalkyl group, ($C_1$–$C_6$) alkoxycarbonyl ($C_1$–$C_6$) alkyl group, ($C_1$–$C_6$) alkylcarbonyl ($C_1$–$C_6$) alkyl group, ($C_1$–$C_6$) alkylcarbonyloxy ($C_1$–$C_6$) alkyl group, phenyl group, substituted phenyl group having 1 to 5, same or different substituents selected from the group consisting of halogen atom, cyano group, nitro group, ($C_1$–$C_6$) alkyl group, halo ($C_1$–$C_6$) alkyl group, ($C_1$–$C_6$) alkoxy group and halo ($C_1$–$C_6$) alkoxy group, phenyl ($C_1$–$C_6$) alkyl group, substituted phenyl ($C_1$–$C_6$) alkyl group having, on the ring thereof, 1 to 5, same or different substituents selected from the group consisting of halogen atom, cyano group, nitro group, ($C_1$–$C_6$) alkyl group, halo ($C_1$–$C_6$) alkyl group, ($C_1$–$C_6$) alkoxy group and halo ($C_1$–$C_6$) alkoxy group, phenoxy ($C_1$–$C_6$) alkyl group, substituted phenoxy ($C_1$–$C_6$) alkyl group having, on the ring thereof, 1 to 5, same or different substituents selected from the group consisting of halogen atom, cyano group, nitro group, ($C_1$–$C_6$) alkyl group, halo ($C_1$–$C_6$) alkyl group, ($C_1$–$C_6$) alkoxy group and halo ($C_1$–$C_6$) alkoxy group, phenylcarbonyloxy ($C_1$–$C_6$) alkyl group, substituted phenylcarbonyloxy ($C_1$–$C_6$) alkyl group having, on the ring thereof, 1 to 5, same or different substituents selected from the group consisting of halogen atom, cyano group, nitro group, ($C_1$–$C_6$) alkyl group, halo ($C_1$–$C_6$) alkyl group, ($C_1$–$C_6$) alkoxy group and halo ($C_1$–$C_6$) alkoxy group or ($C_1$–$C_6$) alkoxycarbonyl group; and $R^2$ represents the following formula (A):

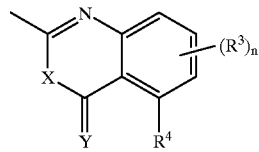

(A)

(wherein $R^3$, which may be same or different, represents halogen atom, cyano group, nitro group, hydroxyl group, ($C_1$–$C_6$) alkyl group, halo ($C_1$–$C_6$) alkyl group, ($C_1$–$C_6$) alkoxy group, halo ($C_1$–$C_6$) alkoxy group or carboxyl group, n represents an integer of 0 to 3, and $R^4$ represents hydrogen atom, halogen atom, cyano group, nitro group, hydroxyl group, ($C_1$–$C_6$) alkyl group, halo ($C_1$–$C_6$) alkyl group, ($C_1$–$C_6$) alkoxy group, halo ($C_1$–$C_6$) alkoxy group or carboxyl group, further, $R^3$ or $R^3$ and $R^4$ may be taken conjointly with a carbon atom of the adjacent phenyl group to form a ($C_1$–$C_6$) alkenylene ring, and X and Y may be same or different and represent oxygen atom or sulfur atom); or the following formula (B):

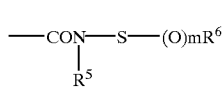

(wherein $R^5$ represents hydrogen atom, $(C_1-C_{20})$ alkyl group, halo $(C_1-C_{20})$ alkyl group, $(C_2-C_{20})$ alkenyl group, halo $(C_2-C_{20})$ alkenyl group, $(C_2-C_{20})$ alkynyl group, halo $(C_2-C_{20})$ alkynyl group, $(C_3-C_7)$ cycloalkyl group, $(C_3-C_7)$ cycloalkenyl group, $(C_1-C_6)$ alkoxy $(C_1-C_6)$ alkyl group, phenyl group, substituted phenyl group having 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group, hydroxyl group, carboxyl group, $(C_1-C_6)$ alkoxycarbonyl group, carbamoyl group and aminocarbonyl group substituted with same or different hydrogen atoms or $(C_1-C_6)$ alkyl groups, phenyl $(C_1-C_6)$ alkyl group, substituted phenyl $(C_1-C_6)$ alkyl group having, on the ring thereof, 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, or a 5- or 6-membered heterocyclic group having at least one, same or different hetero atoms selected from the group consisting of oxygen atom, sulfur atom and nitrogen atom, further, said heterocyclic group may have, on the ring thereof, at least one, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group;

$R^6$ represents $(C_1-C_{20})$ alkyl group, halo $(C_1-C_{20})$ alkyl group, $(C_2-C_{20})$ alkenyl group, halo $(C_2-C_{20})$ alkenyl group, $(C_2-C_{20})$ alkynyl group, halo $(C_2-C_{20})$ alkynyl group, $(C_3-C_7)$ cycloalkyl group, $(C_3-C_7)$ cycloalkenyl group, $(C_1-C_6)$ alkoxy $(C_1-C_6)$ alkyl group, phenyl group, substituted phenyl group having 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, phenyl $(C_1-C_6)$ alkyl group, substituted phenyl $(C_1-C_6)$ alkyl group having, on the ring thereof, 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, a 5- or 6-membered heterocyclic group having at least one, same or different hetero atoms selected from the group consisting of oxygen atom, sulfur atom and nitrogen atom, further, said heterocyclic group may have, on the ring thereof, at least one, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, or

—$N(R^7)R^8$ (wherein $R^7$ and $R^8$, which may be same or different, represent $(C_1-C_{20})$ alkyl group, halo $(C_1-C_{20})$ alkyl group, cyano $(C_1-C_6)$ alkyl group, $(C_2-C_{20})$ alkenyl group, halo $(C_2-C_{20})$ alkenyl group, $(C_2-C_{20})$ alkynyl group, halo $(C_2-C_{20})$ alkynyl group, $(C_3-C_7)$ cycloalkyl group, $(C_3-C_7)$ cycloalkenyl group, $(C_1-C_6)$ alkoxy $(C_1-C_6)$ alkyl group, $(C_1-C_6)$ alkoxy $(C_1-C_6)$ alkoxy $(C_1-C_6)$ alkyl group, $(C_1-C_{12})$ alkylcarbonyl group, halo $(C_1-C_{12})$ alkylcarbonyl group, $(C_1-C_{12})$ alkoxycarbonyl group, $(C_1-C_{12})$ alkoxycarbonyl $(C_1-C_6)$ alkyl group, $(C_3-C_7)$ cycloalkylcarbonyl group, substituted $(C_3-C_7)$ cycloalkylcarbonyl group substituted with at least one, same or different halogen atoms, $(C_2-C_{12})$ alkenyloxycarbonyl group, $(C_2-C_{12})$ alkenyloxycarbonyl $(C_1-C_6)$ alkyl group, $(C_2-C_{12})$ alkynyloxycarbonyl group, $(C_2-C_{12})$ alkynyloxycarbonyl $(C_1-C_6)$ alkyl group, $(C_1-C_6)$ alkoxy $(C_1-C_6)$ alkoxycarbonyl group, $(C_1-C_6)$ alkoxy $(C_1-C_6)$ alkoxycarbonyl $(C_1-C_6)$ alkyl group, di$(C_1-C_{12})$ alkylaminocarbonyl group in which $(C_1-C_{12})$ alkyl groups may be same or different, di$(C_1-C_{12})$ alkylaminocarbonyl $(C_1-C_6)$ alkyl group in which $(C_1-C_{12})$ alkyl groups may be same or different, phenyl group, substituted phenyl group having 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group, hydroxyl group, carboxyl group, $(C_1-C_6)$ alkoxycarbonyl group, carbamoyl group and aminocarbonyl group substituted with same or different hydrogen atoms or $(C_1-C_6)$ alkyl groups, phenyl $(C_1-C_6)$ alkyl group, substituted phenyl $(C_1-C_6)$ alkyl group having, on the ring thereof, 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, phenylcarbonyl group, substituted phenylcarbonyl group having, on the ring thereof, 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, phenoxycarbonyl group, substituted phenoxycarbonyl group having, on the ring thereof, 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, phenyl $(C_1-C_6)$ alkoxycarbonyl group, substituted phenyl $(C_1-C_6)$ alkoxycarbonyl group having, on the ring thereof, 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group and hydroxyl group, phenyl $(C_1-C_6)$ alkoxycarbonyl $(C_1-C_6)$ alkyl group, substituted phenyl $(C_1-C_6)$ alkoxycarbonyl $(C_1-C_6)$ alkyl group having, on the ring thereof, 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo ($C_1$–$C_6$) alkoxy group and hydroxyl group, a 5- or 6-membered heterocyclic group having at least one, same or different hetero atoms selected from the group consisting of oxygen atom, sulfur atom and nitrogen atom, further, said heterocyclic group may have, on the ring thereof, at least one, same or different substituents selected from the group consisting of halogen atom, cyano group, nitro group, ($C_1$–$C_6$) alkyl group, halo ($C_1$–$C_6$) alkyl group, ($C_1$–$C_6$) alkoxy group, halo ($C_1$–$C_6$) alkoxy group and hydroxyl group, or a 5- or 6-membered heterocyclic carbonyl group having at least one, same or different hetero atoms selected from the group consisting of oxygen atom, sulfur atom and nitrogen atom, further, said heterocyclic ring may have, on the ring thereof, at least one, same or different substituents selected from the group consisting of halogen atom, cyano group, nitro group, ($C_1$–$C_6$) alkyl group, halo ($C_1$–$C_6$) alkyl group, ($C_1$–$C_6$) alkoxy group, halo ($C_1$–$C_6$) alkoxy group and hydroxyl group, and alternatively, $R^7$ and $R^8$ may be taken conjointly to form a ($C_2$–$C_6$) alkylene group which may be intercepted by oxygen atom, sulfur atom or —N—$R^9$ (in which $R^9$ represents hydrogen atom, ($C_1$–$C_6$) alkyl group, ($C_1$–$C_6$) alkylcarbonyl group, halo ($C_1$–$C_6$) alkylcarbonyl group, ($C_1$–$C_6$) alkoxycarbonyl group, phenyl group, phenyl ($C_1$–$C_6$) alkyl group or phenyl carbonyl group), further, said alkylene group may be substituted with at least one, same or different substituents selected from the group consisting of ($C_1$–$C_6$) alkyl group, halo ($C_1$–$C_6$) alkyl group, phenyl group, phenyl ($C_1$–$C_6$) alkyl group, oxo group and thioxo group); and m represents an integer of 0 to 2)].

BEST MODE FOR CARRYING OUT THE INVENTION

Definition of the general formula (I) representing the 1,2,3-thiadiazole derivatives of the present invention will be explained below, in which "n-" means normal, "i-" means iso, "s-" means secondary and "t-" means tertiary. In the definition of general formula (I), the term "halogen atom" means chlorine atom, bromine atom, iodine atom or fluorine atom; and the term "($C_1$–$C_{20}$) alkyl group" means a straight or branched chain alkyl group having 1 to 20 carbon atoms such as methyl, ethyl, n-propyl, i-propyl, n-butyl, i-butyl, s-butyl, t-butyl, n-pentyl, neopentyl, n-hexyl, octyl, decyl, hexadecanyl, octadecanyl, eicosanyl and the like.

The term "halo ($C_1$–$C_{20}$) alkyl group" means a straight or branched chain alkyl group having 1 to 20 carbon atoms which may be substituted with at least one, same or different halogen atoms. Examples thereof include chloromethyl, difluoromethyl, trifluoromethyl, bromomethyl, 2-bromoethyl, 1,2-dichloropropyl, 2,2,3,3,3-pentafluoropropyl, 2,3-dibromobutyl, 4-iodobutyl, chlorohexyl, bromodecenyl, iodohexadecanyl, fluoroeicosanyl and the like.

The term "hydroxy ($C_1$–$C_6$) alkyl group" include a straight or branched chain alkyl group having 1 to 6 carbon atoms substituted with at least one hydroxyl groups. Examples thereof include hydroxymethyl, 1,2-dihydroxypropyl and the like. The term "($C_1$–$C_6$) alkoxy group" means a straight or branched chain alkoxy group having 1 to 6 carbon atoms. Examples thereof include methoxy, ethoxy, i-propoxy and the like. The term "($C_1$–$C_6$) alkoxy ($C_1$–$C_6$) alkyl group" means a straight or branched chain alkyl group having 1 to 6 carbon atoms substituted with at least one alkoxy groups having 1 to 6 carbon atoms.

The term "($C_3$–$C_6$) cycloalkyl group" means a cyclic alkyl group having 3 to 6 carbon atoms, of which examples include cyclopropyl, cyclobutyl, cyclopentyl, cyclohexyl and the like.

The term "($C_1$–$C_6$) alkoxy group" means a straight or branched chain alkoxy group having 1 to 6 carbon atoms, of which examples methoxy, ethoxy, i-propoxy and the like.

The term "halo ($C_1$–$C_6$) alkoxy group" means a straight or branched chain alkoxy group having 1 to 6 carbon atoms which may be substituted with at least one, same or different halogen atoms. Examples thereof include trifluoromethoxy, 2-chloroethoxy, 4-bromoethoxy, 4-iodohexyloxy and the like.

The term "($C_2$–$C_{20}$) alkenyl group" means a straight or branched chain alkenyl group having at least one double bonds and 2 to 20 carbon atoms. Examples thereof include vinyl, allyl, isopropenyl, 1-methyl-2-propenyl, 1-butenyl, 2-butenyl, 3-butenyl, pentenyl, hexenyl, hexadecenyl, octadecenyl, eicosenyl and the like. The term "halo ($C_2$–$C_{20}$) alkenyl group" means a straight or branched chain alkenyl group having 2 to 20 carbon atoms, wherein at least one of the hydrogen atoms thereof are substituted with same or different halogen atoms. Examples thereof include 2-chloro-2-propenyl, 2,3-dibromo-2-propenyl, 3,3-dichloro-2-propenyl and the like.

The term "($C_2$–$C_{20}$) alkynyl group" means a straight or branched chain alkynyl group having at least one triple bonds and 2 to 20 carbon atoms. Examples thereof include ethynyl, 2-propynyl, 1-methyl-2-propynyl, 1-butynyl, 2-butynyl, 3-butynyl, hexadec-8-ynyl and the like. The term "halo ($C_2$–$C_{20}$) alkynyl group" means a straight or branched chain alkynyl group having 2 to 20 carbon atoms, wherein at least one of the hydrogen atoms thereof are substituted with same or different halogen atoms. Examples thereof include 2-chloroethynyl, 1-bromo-2-propynyl, 3-iodo-2-propynyl and the like.

The term "($C_1$–$C_6$) alkoxy ($C_1$–$C_6$) alkyl group" means a straight or branched chain alkyl group having 1 to 6 carbon atoms, wherein at least one of the hydrogen atoms thereof are substituted with straight or branched chain alkoxy groups having 1 to 6 carbon atoms. Examples thereof include methoxymethyl, ethoxymethyl, 1-methoxypropyl, 6-methoxyhexyl, 2,3-dimethoxypropyl, 3-methoxy-4-propoxybutyl, 3-(1,2-dimethylpropoxy)-2-methylpropyl and the like. The term "halo ($C_1$–$C_6$) alkoxy ($C_1$–$C_6$) alkyl group" means an ($C_1$–$C_6$) alkoxy ($C_1$–$C_6$) alkyl group, wherein at least one the hydrogen atoms thereof are substituted with halogen atoms.

The term "5- or 6-membered heterocyclic group having at least one, same or different hetero atoms selected from the group consisting of oxygen atom, sulfur atom and nitrogen atom" means a saturated or unsaturated, 5- or 6-membered heterocyclic group. As examples thereof, mention can be made of the substituents derived from heterocyclic ring such as furan, thiophene, pyran, pyrrole, imidazole, pyrazole, isothiazole, isoxazole, pyridine, pyrazine, pyrimidine, pyridazine, 1,2,3-thiadiazole, 1,3,4-thiadiazole, 1,2,4-triazole, 1,2,4-triazine, 1,3,5-triazine, dioxane, dithiolan, 1,3-thiazine, piperidine, piperazine, morpholine and the like.

In the present invention, the following compounds are preferable:

On $R^1$, preferable substituents are ($C_1$–$C_6$) alkyl groups, and particularly preferable substituents are ($C_1$–$C_3$) alkyl groups.

In cases where $R^2$ is represented by the formula (A), preferable substituents are those in which n is zero and $R^4$ is hydrogen atom or halogen atom. In cases where $R^2$ is represented by the formula (B), preferable substituents are those in which $R^5$ is hydrogen atom and $R^6$ is a phenyl group or a substituted phenyl group having 1 to 5, same or different substituents selected from the group consisting of halogen atom, cyano group, nitro group, $(C_1-C_6)$ alkyl group, halo $(C_1-C_6)$ alkyl group, $(C_1-C_6)$ alkoxy group, halo $(C_1-C_6)$ alkoxy group, hydroxyl group, carboxyl group, $(C_1-C_6)$ alkoxycarbonyl group, carbamoyl group and aminocarbonyl group substituted with same or different hydrogen atoms or $(C_1-C_6)$ alkyl group, or —N($R^7$)$R^8$ (in which $R^7$ and $R^8$ may be same or different and represent $(C_1-C_6)$ alkyl group, $(C_1-C_6)$ alkoxycarbonyl $(C_1-C_6)$ alkyl group or $(C_1-C_6)$ alkoxycarbonyl group or $R^7$ and $R^8$, taken conjointly, form a $(C_2-C_6)$ alkylene group which may be intercepted by oxygen atom, sulfur atom or —$NR^9$ (in which $R^9$ represents hydrogen atom, $(C_1-C_6)$ alkyl group, phenyl group, phenyl $(C_1-C_6)$ alkyl group or phenyl carbonyl group), further, said alkylene group may be substituted with at least one, same or different substituents selected from the group consisting of $(C_1-C_6)$ alkyl group, phenyl group, phenyl $(C_1-C_6)$ alkyl group, oxo group and thioxo group).

In the general formula (I) of the present invention, the 1,2,3-thiadiazole derivatives represented by the general formula (I-a) can be produced according to the production process 1 and 2 mentioned below, or the like. Production Process 1: In the case where $R^2$ represents formula (A) and X and Y are oxygen atoms isolating the compound (IV), and then reacting the compound (IV) with an acid anhydride.

Alternatively, it is also possible to produce the compound represented by general formula (I-a-1) directly by reacting a 1,2,3-thiadiazole compound represented by general formula (II) with an anthranilic acid compound represented by general formula (III) in the presence of an inert solvent and a base.

1-1. General Formula (II)→General Formula (IV)

The inert solvent used in this reaction may be any inert solvent so far as it does not obstruct the progress of this reaction markedly. Examples of the inert solvent include alcohols such as methanol, ethanol, propanol, butanol and the like; aromatic hydrocarbons such as benzene, toluene, xylene and the like; halogenated hydrocarbons such as dichloromethane, chloroform, carbon tetrachloride, chlorobenzene and the like; esters such as ethyl acetate and the like; nitriles such as acetonitrile, benzonitrile and the like; acyclic ethers such as methyl cellosolve, diethyl ether and the like; cyclic ethers such as dioxane, tetrahydrofuran and the like; sulfolane, dimethyl sulfone, dimethyl sulfoxide, water, and the like. These inert solvents can be used either alone or in the form of a mixture of two or more.

As said base used in this reaction, inorganic bases and organic bases can be referred to. The inorganic bases include alkali metal hydroxides such as sodium hydroxide, potassium hydroxide and the like, alkali metal carbonates, and the like. The organic bases include tertiary amines such as triethylamine and the like, and pyridines. These bases can be used in an amount appropriately selected in the range of from equimolar to excessive molar quantities to the 1,2,3-thiadiazole represented by general formula (II).

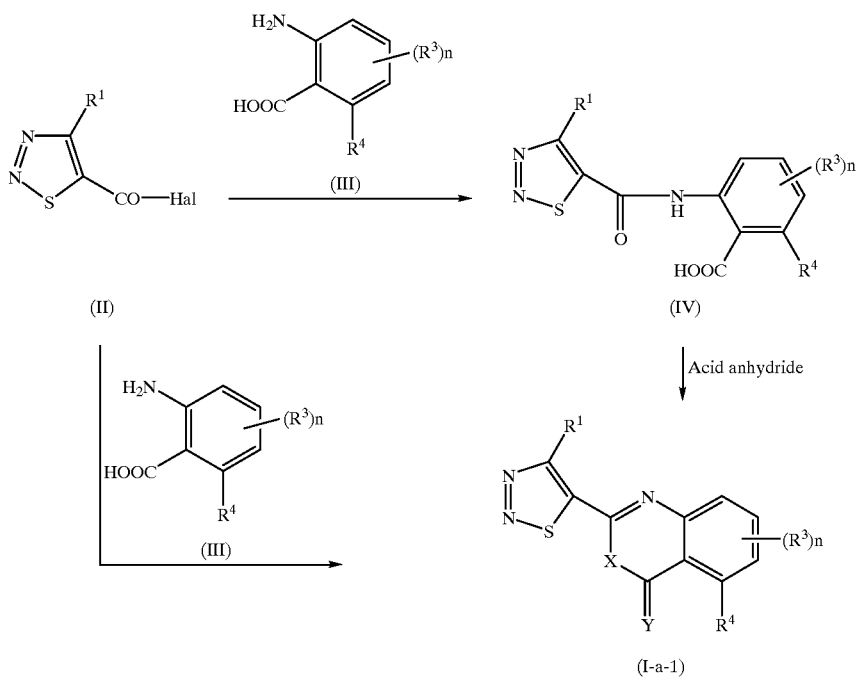

wherein $R^1$, $R^3$, $R^4$ and n are as defined above and Hal represents a halogen atom.

The 1,2,3-thiadiazole derivative represented by general formula (I-a-1) can be produced by reacting a 1,2,3-thiadiazole compound represented by general formula (II) with an anthranilic acid compound represented by general formula (III) in the presence of an inert solvent and a base to form a compound represented by general formula (IV), The reaction temperature may be a temperature falling in the range of from room temperature to the boiling point of the inert solvent used. Although the reaction time varies with the scale of reaction and the reaction temperature, it is from several minutes to 48 hours.

After completion of the reaction, the compound represented by general formula (IV) is isolated from the reaction system containing the objective product, and a purification may be practiced, if desired. Alternatively, the reaction mixture may directly be used in the subsequent step of the reaction without isolating the compound of general formula (IV).

The compound represented by general formula (II) can be produced according to the method described in JP-A-8-325110.

1-2. General Formula (IV)→General formula (I-a-1)

This reaction is a cyclization reaction. If the reactant (acid anhydride) is used in an excessive amount, the acid anhydride can be made to serve not only as a reactant but also as an inert solvent.

The reaction temperature may be in the range of from room temperature to the boiling point of the inert solvent used. It is preferable to carry out the reaction in the boiling temperature zone of the inert solvent used.

Although the reaction time may vary with scale and temperature of the reaction, it is from several minutes to 48 hours.

After completion of the reaction, the 1,2,3-thiadiazole derivative represented by general formula (I-a-1) is isolated from the reaction system containing the objective product in the conventional manner. If desired, a purification may be carried out.

1-3. General Formula (II)→General Formula (I-a-1)

According to this reaction, the 1,2,3-thiadiazole derivative represented by general formula (I-a-1) can be produced in the same manner as in Reaction 1-1. A direct production can be practiced by prolonging the reaction time.

Production Process 2: In the case where $R^2$ represents formula (A) and X and Y are sulfur atoms

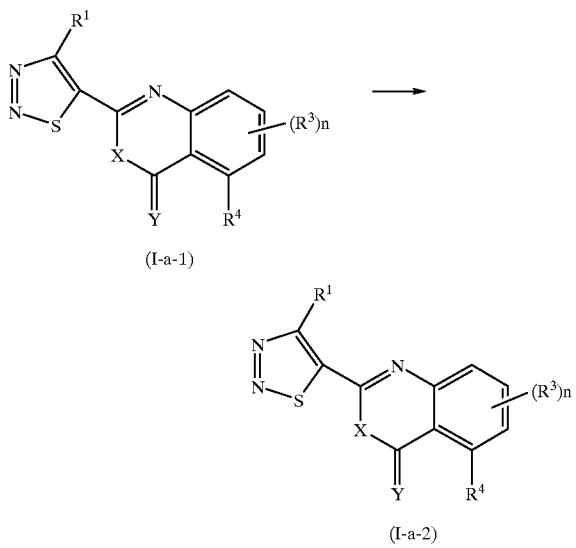

wherein $R^1$, $R^3$, $R^4$ and n are as defined above.

A 1,2,3-benzothiadiazole derivative represented by general formula (I-a-2) can be produced by reacting a 1,2,3-thiadiazole derivative represented by general formula (I-a-1) with a sulfurizing agent such as Lauesson's reagent, $P_4S_{10}$ or the like in the presence of an inert solvent.

The inert solvent which can be used in this reaction is the same as those used in the Production Process 1-1.

The amount of the sufurizing agent such as Lauesson's reagent, $P_4S_{10}$ or the like may be appropriately selected in the range of from an equimolar quantity to the 1,2,3-thiadiazole derivative of general formula (I-a-1) to a largely excessive quantity. Preferably, the sulfurizing agent is used in a largely excessive quantity.

The reaction temperature is in the range from room temperature to the boiling temperature zone of the inert solvent used. Although the reaction time may vary with scale and temperature of the reaction, it is from several minutes to 48 hours.

After completion of the reaction, the compound represented by general formula (I-a-2) is isolated from the reaction system containing the objective product in the usual manner. If desired, a purification may be carried out.

This production method can be put into practice according to the description of Heterocycles, 19, 2093 (1882), etc.

Among the compounds represented by general formula (I) of the present invention, the 1,2,3-thiadiazole derivatives represented by general formula (I-b) can be produced, for example, by the production methods exemplified below.

Production Process 3: In the case where $R^2$ represents formula (B)

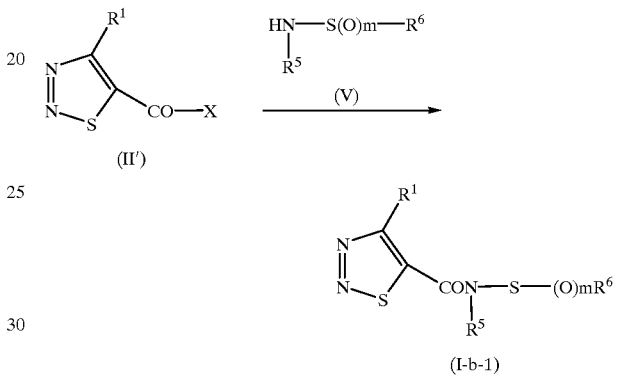

wherein $R^1$, $R^5$, $R^6$ and m are as defined above and X represents a leaving group.

A 1,2,3-thiadiazole derivative represented by general formula (I-b-1) can be produced by reacting a compound represented by general formula (II') with a compound represented by general formula (V) in the presence of an inert solvent and a base.

The solvent used in this reaction may be any solvents, so far as they do not disturb the progress of the reaction. Examples of the solvent include alcohols such as methanol, ethanol, propanol, butanol and the like, aromatic hydrocarbons such as benzene, toluene, xylene and the like, halogenated hydrocarbons such as dichloromethane, chloroform, carbon tetrachloride, chlorobenzene and the like, esters such as ethyl acetate and the like, nitrites such as acetonitrile, benzonitrile and the like, acyclic ethers such as methyl cellosolve, diethyl ether and the like, cyclic ethers such as dioxane, tetrahydrofuran and the like, sulfolane, dimethyl sulfone, dimethyl sulfoxide, water, and the like. These inert solvents may be used either alone or in the form of a mixture of two or more.

As the base, inorganic and organic bases can be used. The inorganic bases include alkali hydroxides such as sodium hydroxide, potassium hydroxide and the like and alkali carbonates; and the organic bases include tertiary amines such as triethylamine and the like, pyridines and the like. These bases are used in an appropriate amount falling in the range of from an equimolar quantity to the 1,2,3-thiadiazole compound represented by general formula (II') to an excessive molar quantity.

Since this reaction is an equimolar reaction, the compound of formula (II') and the compound of formula (V) may be used in equimolar quantities. It is also possible, however, to used any one of the reactants in an excessive quantity.

The reaction temperature is in the range of from room temperature to the boiling temperature zone of the inert solvent. Although the reaction time may vary with scale and temperature of the reaction, it is from several minutes to 48 hours.

After completion of the reaction, the 1,2,3-thiadiazole derivative represented by general formula (I-b-1) is isolated from the reaction system containing the objective product in the usual manner. If desired, a purification may be carried out.

Production Process 4: In the case where $R^2$ represents formula (B)

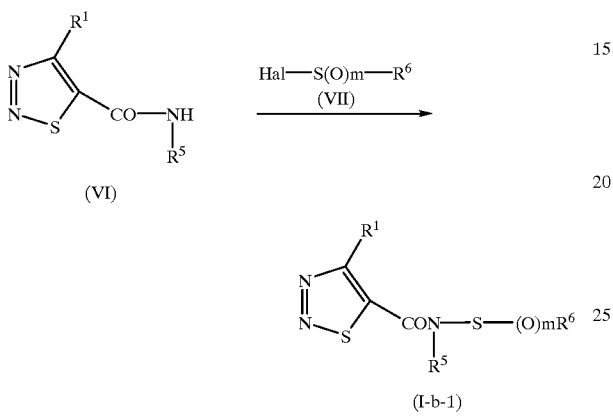

wherein $R^1$, $R^5$, $R^6$ and m are as defined above and Hal represents halogen atom.

A 1,2,3-thiadiazole derivative represented by general formula (I-b-1) can be produced by reacting a compound represented by general formula (VI) with a compound represented by general formula (VII) in the presence of an inert solvent and a base.

This reaction can be carried out according to the description of "Shin Jikken Kagaku Koza", 14-III, Page 1803 (published by Maruzen K. K.), etc. Production Process 5: In the case where $R^2$ represents formula (B) and $R^6$ represents $-N(R^7)R^8$ 5-1.

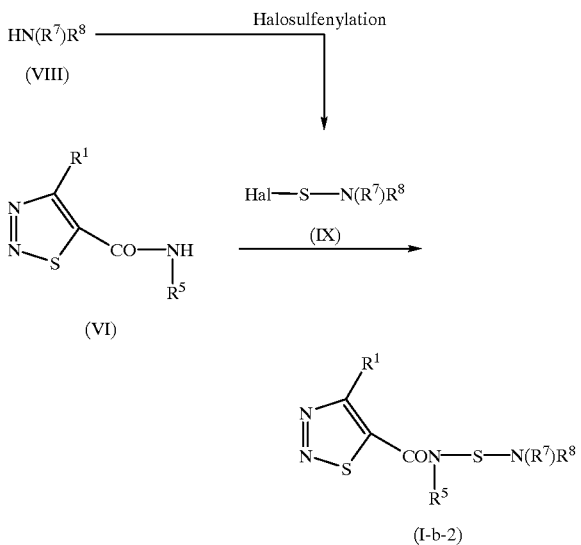

wherein $R^1$, $R^5$, $R^7$, $R^8$ and Hal are as defined above.

A 1,2,3-thiadiazole derivative represented by general formula (I-b-2) can be produced by halosulfenylating an amine represented by general formula (VIII) with sulfur monochloride, sulfur dichloride or the like to obtain a compound represented by general formula (IX), followed by reacting the thus formed compound (IX) with a compound represented by general formula (VI) in the presence of a base and an inert solvent.

5-2.

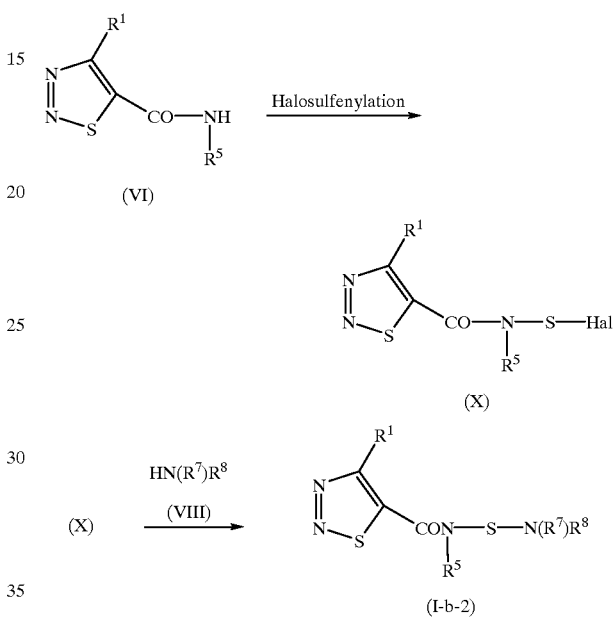

wherein $R^1$, $R^5$, $R^7$, $R^8$ and Hal are as defined above.

A 1,2,3-thiadiazole derivative represented by general formula (I-b-2) can be produced by treating a compound represented by general formula (VI) in the same manner as in 5-1 to obtain a compound represented by general formula (X), isolating or not isolating the thus formed compound (X), and then reacting the compound (X) with an amine represented by general formula (VIII) in the presence of a base and an inert solvent.

The reactions of 5-1 and 5-2 can be carried out according to the procedure disclosed in JP-A-58-26804, etc.

The compounds represented by general formula (II') and general formula (VI) can be produced according to the procedure described in JP-A-8-325110, etc.

Next, typical examples of the 1,2,3-thiadiazole derivatives represented by general formula (I) are shown below. The invention is by no means limited by these compounds. In Table 1 are shown the compounds represented by general formula (I-a). In Table 2 are shown the compounds represented by general formula (I-b).

General formula (I-a)

TABLE 1

(I-a)

| No. | R¹ | (R³)n, R⁴ | X | Y | Property |
|---|---|---|---|---|---|
| a 1 | H | H | O | O | |
| a 2 | H | 5-F | O | O | |
| a 3 | H | 6-F | O | O | |
| a 4 | H | 7-F | O | O | |
| a 5 | H | 8-F | O | O | |
| a 6 | H | 5-Cl | O | O | |
| a 7 | H | 6-Cl | O | O | |
| a 8 | H | 7-Cl | O | O | |
| a 9 | H | 8-Cl | O | O | |
| a 10 | H | 6-Br | O | O | |
| a 11 | H | 6,8-Br₂ | O | O | |
| a 12 | H | 6-I | O | O | |
| a 13 | H | 6,8-I₂ | O | O | |
| a 14 | H | 5-CH₃ | O | O | |
| a 15 | H | 6-CH₃ | O | O | |
| a 16 | H | 7-CH₃ | O | O | |
| a 17 | H | 8-CH₃ | O | O | |
| a 18 | H | 6,8-(CH₃)₂ | O | O | |
| a 19 | H | 6-NO₂ | O | O | |
| a 20 | H | 7-NO₂ | O | O | |
| a 21 | H | 6-OH | O | O | |
| a 22 | H | 8-OH | O | O | |
| a 23 | H | 8-OCH₃ | O | O | |
| a 24 | H | 6,7-(OCH₃)₂ | O | O | |
| a 25 | H | 7-COOH | O | O | |
| a 26 | H | 6-CH=CH—CH=CH-7 | O | O | |
| a 27 | CH₃ | H | O | O | m.p. 167° C. |
| a 28 | CH₃ | 5-F | O | O | m.p. 176–177° C. |
| a 29 | CH₃ | 6-F | O | O | |
| a 30 | CH₃ | 7-F | O | O | |
| a 31 | CH₃ | 8-F | O | O | |
| a 32 | CH₃ | 5-Cl | O | O | |
| a 33 | CH₃ | 6-Cl | O | O | m.p. 151° C. |
| a 34 | CH₃ | 7-Cl | O | O | |
| a 35 | CH₃ | 8-Cl | O | O | |
| a 36 | CH₃ | 6-Br | O | O | |
| a 37 | CH₃ | 6,8-Br₂ | O | O | |
| a 38 | CH₃ | 6-I | O | O | |
| a 39 | CH₃ | 6,8-I₂ | O | O | |
| a 40 | CH₃ | 5-CH₃ | O | O | m.p. 193° C. |
| a 41 | CH₃ | 6-CH₃ | O | O | |
| a 42 | CH₃ | 7-CH₃ | O | O | |
| a 43 | CH₃ | 8-CH₃ | O | O | m.p. 174° C. |
| a 44 | CH₃ | 6,8-(CH₃)₂ | O | O | |
| a 45 | CH₃ | 7-CF₃ | O | O | |
| a 46 | CH₃ | 6-NO₂ | O | O | |
| a 47 | CH₃ | 7-NO₂ | O | O | |
| a 48 | CH₃ | 6-OH | O | O | |
| a 49 | CH₃ | 8-OH | O | O | |
| a 50 | CH₃ | 5-OCH₃ | O | O | |
| a 51 | CH₃ | 6,7-(OCH₃)₂ | O | O | |
| a 52 | CH₃ | 7-CN | O | O | |
| a 53 | CH₃ | 7-COOH | O | O | |
| a 54 | CH₃ | 6-CH=CH—CH=CH-7 | O | O | |
| a 55 | C₂H₅ | H | O | O | m.p. 99° C. |
| a 56 | C₂H₅ | 5-F | O | O | |
| a 57 | C₂H₅ | 6-F | O | O | |
| a 58 | C₂H₅ | 7-F | O | O | |
| a 59 | C₂H₅ | 8-F | O | O | |
| a 60 | C₂H₅ | 5-Cl | O | O | |
| a 61 | C₂H₅ | 6-Cl | O | O | |
| a 62 | C₂H₅ | 7-Cl | O | O | |
| a 63 | C₂H₅ | 8-Cl | O | O | |
| a 64 | C₂H₅ | 6-Br | O | O | |
| a 65 | C₂H₅ | 6,8-Br₂ | O | O | |
| a 66 | C₂H₅ | 6-I | O | O | |
| a 67 | C₂H₅ | 6,8-I₂ | O | O | |
| a 68 | C₂H₅ | 5-CH₃ | O | O | |
| a 69 | C₂H₅ | 6-CH₃ | O | O | |
| a 70 | C₂H₅ | 7-CH₃ | O | O | |
| a 71 | C₂H₅ | 8-CH₃ | O | O | |
| a 72 | C₂H₅ | 6,8-(CH₃)₂ | O | O | |
| a 73 | C₂H₅ | 6-NO₂ | O | O | |
| a 74 | C₂H₅ | 7-NO₂ | O | O | |
| a 75 | C₂H₅ | 6-OH | O | O | |
| a 76 | C₂H₅ | 8-OH | O | O | |
| a 77 | C₂H₅ | 8-OCH₃ | O | O | |
| a 78 | C₂H₅ | 6,7-(OCH₃)₂ | O | O | |
| a 79 | C₂H₅ | 7-COOH | O | O | |
| a 80 | C₂H₅ | 6-CH=CH—CH=CH-7 | O | O | |
| a 81 | n-C₃H₇ | H | O | O | |
| a 82 | n-C₃H₇ | 5-F | O | O | |
| a 83 | n-C₃H₇ | 6-F | O | O | |
| a 84 | n-C₃H₇ | 7-F | O | O | |
| a 85 | n-C₃H₇ | 8-F | O | O | |
| a 86 | n-C₃H₇ | 5-Cl | O | O | |
| a 87 | n-C₃H₇ | 6-Cl | O | O | |
| a 88 | n-C₃H₇ | 7-Cl | O | O | |
| a 89 | n-C₃H₇ | 8-Cl | O | O | |
| a 90 | n-C₃H₇ | 6-Br | O | O | |
| a 91 | n-C₃H₇ | 6,8-Br₂ | O | O | |
| a 92 | n-C₃H₇ | 6-I | O | O | |
| a 93 | n-C₃H₇ | 6,8-I₂ | O | O | |
| a 94 | n-C₃H₇ | 5-CH₃ | O | O | |
| a 95 | n-C₃H₇ | 6-CH₃ | O | O | |
| a 96 | n-C₃H₇ | 7-CH₃ | O | O | |
| a 97 | n-C₃H₇ | 8-CH₃ | O | O | |
| a 98 | n-C₃H₇ | 6,8-(CH₃)₂ | O | O | |
| a 99 | n-C₃H₇ | 6-NO₂ | O | O | |
| a 100 | n-C₃H₇ | 7-NO₂ | O | O | |
| a 101 | n-C₃H₇ | 6-OH | O | O | |
| a 102 | n-C₃H₇ | 8-OH | O | O | |
| a 103 | n-C₃H₇ | 8-OCH₃ | O | O | |
| a 104 | n-C₃H₇ | 6,7-(OCH₃)₂ | O | O | |
| a 105 | n-C₃H₇ | 7-COOH | O | O | |
| a 106 | n-C₃H₇ | 6-CH=CH—CH=CH-7 | O | O | |
| a 107 | i-C₃H₇ | H | O | O | m.p. 145° C. |
| a 108 | i-C₃H₇ | 5-F | O | O | |
| a 109 | i-C₃H₇ | 6-F | O | O | |
| a 110 | i-C₃H₇ | 7-F | O | O | |
| a 111 | i-C₃H₇ | 8-F | O | O | |
| a 112 | i-C₃H₇ | 5-Cl | O | O | |
| a 113 | i-C₃H₇ | 6-Cl | O | O | |
| a 114 | i-C₃H₇ | 7-Cl | O | O | |
| a 115 | i-C₃H₇ | 8-Cl | O | O | |
| a 116 | i-C₃H₇ | 6-Br | O | O | |
| a 117 | i-C₃H₇ | 6,8-Br₂ | O | O | |
| a 118 | i-C₃H₇ | 6-I | O | O | |
| a 119 | i-C₃H₇ | 6,8-I₂ | O | O | |

TABLE 1-continued (I-a)

| No. | $R^1$ | $(R^3)n, R^4$ | X | Y | Property |
|---|---|---|---|---|---|
| a 120 | i-$C_3H_7$ | 5-$CH_3$ | O | O | |
| a 121 | i-$C_3H_7$ | 6-$CH_3$ | O | O | |
| a 122 | i-$C_3H_7$ | 7-$CH_3$ | O | O | |
| a 123 | i-$C_3H_7$ | 8-$CH_3$ | O | O | |
| a 124 | i-$C_3H_7$ | 6,8-$(CH_3)_2$ | O | O | |
| a 125 | i-$C_3H_7$ | 6-$NO_2$ | O | O | |
| a 126 | i-$C_3H_7$ | 7-$NO_2$ | O | O | |
| a 127 | i-$C_3H_7$ | 6-OH | O | O | |
| a 128 | i-$C_3H_7$ | 8-OH | O | O | |
| a 129 | i-$C_3H_7$ | 8-$OCH_3$ | O | O | |
| a 130 | i-$C_3H_7$ | 6,7-$(OCH_3)_2$ | O | O | |
| a 131 | i-$C_3H_7$ | 7-COOH | O | O | |
| a 132 | i-$C_3H_7$ | 6-CH=CH—CH=CH-7 | O | O | |
| a 133 | t-$C_4H_9$ | H | O | O | |
| a 134 | t-$C_4H_9$ | 5-F | O | O | |
| a 135 | t-$C_4H_9$ | 6-F | O | O | |
| a 136 | t-$C_4H_9$ | 7-F | O | O | |
| a 137 | t-$C_4H_9$ | 8-F | O | O | |
| a 138 | t-$C_4H_9$ | 5-Cl | O | O | |
| a 139 | t-$C_4H_9$ | 6-Cl | O | O | |
| a 140 | t-$C_4H_9$ | 7-Cl | O | O | |
| a 141 | t-$C_4H_9$ | 8-Cl | O | O | |
| a 142 | t-$C_4H_9$ | 6-Br | O | O | |
| a 143 | t-$C_4H_9$ | 6,8-$Br_2$ | O | O | |
| a 144 | t-$C_4H_9$ | 6-I | O | O | |
| a 145 | t-$C_4H_9$ | 6,8-$I_2$ | O | O | |
| a 146 | t-$C_4H_9$ | 5-$CH_3$ | O | O | |
| a 147 | t-$C_4H_9$ | 6-$CH_3$ | O | O | |
| a 148 | t-$C_4H_9$ | 7-$CH_3$ | O | O | |
| a 149 | t-$C_4H_9$ | 8-$CH_3$ | O | O | |
| a 150 | t-$C_4H_9$ | 6,8-$(CH_3)_2$ | O | O | |
| a 151 | t-$C_4H_9$ | 6-$NO_2$ | O | O | |
| a 152 | t-$C_4H_9$ | 7-$NO_2$ | O | O | |
| a 153 | t-$C_4H_9$ | 6-OH | O | O | |
| a 154 | t-$C_4H_9$ | 8-OH | O | O | |
| a 155 | t-$C_4H_9$ | 8-$OCH_3$ | O | O | |
| a 156 | t-$C_4H_9$ | 6,7-$(OCH_3)_2$ | O | O | |
| a 157 | t-$C_4H_9$ | 7-COOH | O | O | |
| a 158 | t-$C_4H_9$ | 6-CH=CH—CH=CH-7 | O | O | |
| a 159 | c-$C_3H_5$ | H | O | O | |
| a 160 | c-$C_3H_5$ | 5-F | O | O | |
| a 161 | c-$C_3H_5$ | 6-F | O | O | |
| a 162 | c-$C_3H_5$ | 7-F | O | O | |
| a 163 | c-$C_3H_5$ | 8-F | O | O | |
| a 164 | c-$C_3H_5$ | 5-Cl | O | O | |
| a 165 | c-$C_3H_5$ | 6-Cl | O | O | |
| a 166 | c-$C_3H_5$ | 7-Cl | O | O | |
| a 167 | c-$C_3H_5$ | 8-Cl | O | O | |
| a 168 | c-$C_3H_5$ | 6-Br | O | O | |
| a 169 | c-$C_3H_5$ | 6,8-$Br_2$ | O | O | |
| a 170 | c-$C_3H_5$ | 6-I | O | O | |
| a 171 | c-$C_3H_5$ | 6,8-$I_2$ | O | O | |
| a 172 | c-$C_3H_5$ | 5-$CH_3$ | O | O | |
| a 173 | c-$C_3H_5$ | 6-$CH_3$ | O | O | |
| a 174 | c-$C_3H_5$ | 7-$CH_3$ | O | O | |
| a 175 | c-$C_3H_5$ | 8-$CH_3$ | O | O | |
| a 176 | c-$C_3H_5$ | 6,8-$(CH_3)_2$ | O | O | |
| a 177 | c-$C_3H_5$ | 6-$NO_2$ | O | O | |
| a 178 | c-$C_3H_5$ | 7-$NO_2$ | O | O | |
| a 179 | c-$C_3H_5$ | 6-OH | O | O | |
| a 180 | c-$C_3H_5$ | 8-OH | O | O | |
| a 181 | c-$C_3H_5$ | 8-$OCH_3$ | O | O | |
| a 182 | c-$C_3H_5$ | 6,7-$(OCH_3)_2$ | O | O | |
| a 183 | c-$C_3H_5$ | 7-COOH | O | O | |
| a 184 | c-$C_3H_5$ | 6-CH=CH—CH=CH-7 | O | O | |
| a 185 | c-$C_6H_{11}$ | H | O | O | |
| a 186 | c-$C_6H_{11}$ | 5-F | O | O | |
| a 187 | c-$C_6H_{11}$ | 6-F | O | O | |
| a 188 | c-$C_6H_{11}$ | 7-F | O | O | |
| a 189 | c-$C_6H_{11}$ | 8-F | O | O | |
| a 190 | c-$C_6H_{11}$ | 5-Cl | O | O | |
| a 191 | c-$C_6H_{11}$ | 6-Cl | O | O | |
| a 192 | c-$C_6H_{11}$ | 7-Cl | O | O | |
| a 193 | c-$C_6H_{11}$ | 8-Cl | O | O | |
| a 194 | c-$C_6H_{11}$ | 6-Br | O | O | |
| a 195 | c-$C_6H_{11}$ | 6,8-$Br_2$ | O | O | |
| a 196 | c-$C_6H_{11}$ | 6-I | O | O | |
| a 197 | c-$C_6H_{11}$ | 6,8-$I_2$ | O | O | |
| a 198 | c-$C_6H_{11}$ | 5-$CH_3$ | O | O | |
| a 199 | c-$C_6H_{11}$ | 6-$CH_3$ | O | O | |
| a 200 | c-$C_6H_{11}$ | 7-$CH_3$ | O | O | |
| a 201 | c-$C_6H_{11}$ | 8-$CH_3$ | O | O | |
| a 202 | c-$C_6H_{11}$ | 6,8-$(CH_3)_2$ | O | O | |
| a 203 | c-$C_6H_{11}$ | 6-$NO_2$ | O | O | |
| a 204 | c-$C_6H_{11}$ | 7-$NO_2$ | O | O | |
| a 205 | c-$C_6H_{11}$ | 6-OH | O | O | |
| a 206 | c-$C_6H_{11}$ | 8-OH | O | O | |
| a 207 | c-$C_6H_{11}$ | 8-$OCH_3$ | O | O | |
| a 208 | c-$C_6H_{11}$ | 6,7-$(OCH_3)_2$ | O | O | |
| a 209 | c-$C_6H_{11}$ | 7-COOH | O | O | |
| a 210 | c-$C_6H_{11}$ | 6-CH=CH—CH=CH-7 | O | O | |
| a 211 | $CH_2Cl$ | H | O | O | m.p. 139–140° C. |
| a 212 | $CH_2Cl$ | 5-Cl | O | O | |
| a 213 | $CH_2Cl$ | 6-Br | O | O | |
| a 214 | $CH_2Cl$ | 6-$CH_3$ | O | O | |
| a 215 | $CF_3$ | H | O | O | |
| a 216 | $CF_3$ | 5-Cl | O | O | |
| a 217 | $CF_3$ | 6-Br | O | O | |
| a 218 | $CF_3$ | 6-$CH_3$ | O | O | |
| a 219 | $CH_2$—Ph | H | O | O | |
| a 220 | Ph | H | O | O | |
| a 221 | 4-Cl—Ph | H | O | O | |
| a 222 | 4-$NO_2$—Ph | H | O | O | m.p. 227–233° C. |
| a 223 | $CH_2OCH_3$ | H | O | O | m.p. 136–138° C. |
| a 224 | $CH_2O$—Ph | H | O | O | |
| a 225 | $CH_2O$-(2-Cl—Ph) | H | O | O | m.p. 164° C. |
| a 226 | $CH_2O$-(3-Cl—Ph) | H | O | O | |
| a 227 | $CH_2O$-(4-Cl—Ph) | H | O | O | |
| a 228 | $CH_2O$-(4-$CH_3$—Ph) | H | O | O | m.p. 108° C. |
| a 229 | $CH_2O$-(3-$CF_3$—Ph) | H | O | O | m.p. 103° C. |
| a 230 | $CH_2O$-(4-$CH_3O$—Ph) | H | O | O | m.p. 114–117° C. |
| a 231 | $CH_2O$-(4-$NO_2$—Ph) | H | O | O | m.p. 178–179° C. |
| a 232 | $CH_2OH$ | H | O | O | |
| a 233 | $CH_2OCOCH_3$ | H | O | O | m.p. 130° C. |
| a 234 | $CH_2OCO$—Ph | H | O | O | |
| a 235 | $COOCH_3$ | H | O | O | |
| a 236 | $COOC_2H_5$ | H | O | O | m.p. 129– |

TABLE 1-continued (I-a)

| No. | R¹ | (R³)n, R⁴ | X | Y | Property |
|---|---|---|---|---|---|
| a 237 | COOC$_3$H$_7$-n | H | O | O | 130° C. |
| a 238 | COOC$_3$H$_7$-i | H | O | O | |
| a 239 | COOC$_4$H$_9$-i | H | O | O | |
| a 240 | CH$_3$ | H | S | S | Paste |

In Table 1, "c-" represents an alicyclic monocyclic hydrocarbon group, and "Ph" represents a phenyl group. In some of the compounds, the property was pasty. Nuclear magnetic resonance data of these compounds are shown below.

| No. | $^1$HNMR δ value (ppm), solvent CDCl$_3$, TMS as standard substance |
|---|---|
| a 240 | 3.878 (s, 3H), 7.022 (m, 2H), 8.096 (m, 1H), 9.254 (m, 1H) |

In the table, TMS means tetramethylsilane.

Next, typical examples of the 1,2,3-thiadiazole derivatives represented by general formula (I-b) are shown below. The present invention is by no means limited by these compounds.

General formula (I-b)

TABLE 2

(I-b)

| No. | R¹ | R⁵ | R⁶ | m | Property |
|---|---|---|---|---|---|
| b 1 | H | H | CH$_3$ | 0 | |
| b 2 | H | H | i-C$_3$H$_7$ | 0 | |
| b 3 | H | H | Ph | 0 | |
| b 4 | H | H | CH$_2$Ph | 0 | |
| b 5 | H | H | N(CH$_3$)$_2$ | 0 | |
| b 6 | H | H | N(CH$_3$)CO$_2$CH$_3$ | 0 | |
| b 7 | H | H | N(CH$_3$)CO$_2$C$_4$H$_9$-n | 0 | |
| b 8 | H | H | N(i-C$_3$H$_7$)CO$_2$CH$_3$ | 0 | |
| b 9 | H | H | N(n-C$_4$H$_9$)$_2$ | 0 | |
| b 10 | H | H | N(CH$_2$Ph)CH$_2$CH$_2$CO$_2$C$_2$H$_5$ | 0 | |
| b 11 | H | H | Morpholino | 0 | |
| b 12 | H | CH$_3$ | CH$_3$ | 0 | |
| b 13 | H | CH$_3$ | i-C$_3$H$_7$ | 0 | |
| b 14 | H | CH$_3$ | Ph | 0 | |
| b 15 | H | CH$_3$ | CH$_2$Ph | 0 | |
| b 16 | H | CH$_3$ | N(CH$_3$)$_2$ | 0 | |
| b 17 | H | CH$_3$ | N(CH$_3$)CO$_2$CH$_3$ | 0 | |
| b 18 | H | CH$_3$ | N(CH$_3$)CO$_2$C$_4$H$_9$-n | 0 | |
| b 19 | H | CH$_3$ | N(i-C$_3$H$_7$)CO$_2$CH$_3$ | 0 | |
| b 20 | H | CH$_3$ | N(n-C$_4$H$_9$)$_2$ | 0 | |
| b 21 | H | CH$_3$ | N(CH$_2$Ph)CH$_2$CH$_2$CO$_2$C$_2$H$_5$ | 0 | |
| b 22 | H | CH$_3$ | Morpholino | 0 | |
| b 23 | CH$_3$ | H | CH$_3$ | 0 | |
| b 24 | CH$_3$ | H | i-C$_3$H$_7$ | 0 | |
| b 25 | CH$_3$ | H | Ph | 0 | |
| b 26 | CH$_3$ | H | CH$_2$Ph | 0 | |
| b 27 | CH$_3$ | H | N(CH$_3$)$_2$ | 0 | |
| b 28 | CH$_3$ | H | N(CH$_3$)CO$_2$CH$_3$ | 0 | |
| b 29 | CH$_3$ | H | N(CH$_3$)CO$_2$C$_4$H$_9$-n | 0 | |
| b 30 | CH$_3$ | H | N(i-C$_3$H$_7$)CO$_2$CH$_3$ | 0 | |
| b 31 | CH$_3$ | H | N(n-C$_4$H$_9$)$_2$ | 0 | |
| b 32 | CH$_3$ | H | N(CH$_2$Ph)CH$_2$CH$_2$CO$_2$C$_2$H$_5$ | 0 | |
| b 33 | CH$_3$ | H | Morpholino | 0 | |
| b 34 | CH$_3$ | CH$_3$ | CH$_3$ | 0 | |
| b 35 | CH$_3$ | CH$_3$ | i-C$_3$H$_7$ | 0 | |

TABLE 2-continued (I-b)

$$\text{thiadiazole-CON(R}^5\text{)-S-(O)}_m\text{R}^6 \text{ with } R^1$$

| No. | $R^1$ | $R^5$ | $R^6$ | m | Property |
|---|---|---|---|---|---|
| b 36 | $CH_3$ | $CH_3$ | n-$C_6H_{13}$ | 0 | |
| b 37 | $CH_3$ | $CH_3$ | $CH_2CH_2Br$ | 0 | |
| b 38 | $CH_3$ | $CH_3$ | $(CH_2)_3CH_2Br$ | 0 | |
| b 39 | $CH_3$ | $CH_3$ | Ph | 0 | |
| b 40 | $CH_3$ | $CH_3$ | 4-Cl—Ph | 0 | |
| b 41 | $CH_3$ | $CH_3$ | 2,4-$Cl_2$—Ph | 0 | |
| b 42 | $CH_3$ | $CH_3$ | 2-$CH_3$—Ph | 0 | |
| b 43 | $CH_3$ | $CH_3$ | $CH_2Ph$ | 0 | |
| b 44 | $CH_3$ | $CH_3$ | $N(CH_3)_2$ | 0 | |
| b 45 | $CH_3$ | $CH_3$ | $N(CH_3)C_2H_5$ | 0 | |
| b 46 | $CH_3$ | $CH_3$ | $N(CH_3)C_3H_7$-n | 0 | |
| b 47 | $CH_3$ | $CH_3$ | $N(CH_3)C_3H_7$-i | 0 | |
| b 48 | $CH_3$ | $CH_3$ | $N(CH_3)C_4H_9$-n | 0 | |
| b 49 | $CH_3$ | $CH_3$ | $N(CH_3)C_8H_{17}$-n | 0 | |
| b 50 | $CH_3$ | $CH_3$ | $N(CH_3)CH_2Ph$ | 0 | |
| b 51 | $CH_3$ | $CH_3$ | $N(CH_3)CH_2(4$-Cl—Ph$)$ | 0 | |
| b 52 | $CH_3$ | $CH_3$ | $N(CH_3)Ph$ | 0 | |
| b 53 | $CH_3$ | $CH_3$ | $N(CH_3)(3$-$CH_3$—Ph$)$ | 0 | |
| b 54 | $CH_3$ | $CH_3$ | $N(CH_3)CO_2CH_3$ | 0 | |
| b 55 | $CH_3$ | $CH_3$ | $N(CH_3)CO_2C_2H_5$ | 0 | |
| b 56 | $CH_3$ | $CH_3$ | $N(CH_3)CO_2C_3H_7$-n | 0 | |
| b 57 | $CH_3$ | $CH_3$ | $N(CH_3)CO_2C_3H_7$-i | 0 | |
| b 58 | $CH_3$ | $CH_3$ | $N(CH_3)CO_2C_4H_9$-n | 0 | |
| b 59 | $CH_3$ | $CH_3$ | $N(CH_3)CO_2CH_2CH_2OC_2H_5$ | 0 | |
| b 60 | $CH_3$ | $CH_3$ | $N(CH_3)CO_2CH_2CH_2OPh$ | 0 | |
| b 61 | $CH_3$ | $CH_3$ | $N(CH_3)CO_2(CH_2CH_2O)_2C_4H_6$-n | 0 | |
| b 62 | $CH_3$ | $CH_3$ | $N(CH_3)CH_2CO_2CH_3$ | 0 | |
| b 63 | $CH_3$ | $CH_3$ | $N(CH_3)CH_2CH_2CO_2C_2H_5$ | 0 | |
| b 64 | $CH_3$ | $CH_3$ | $N(CH_3)COCH_3$ | 0 | |
| b 65 | $CH_3$ | $CH_3$ | $N(CH_3)COPh$ | 0 | |
| b 66 | $CH_3$ | $CH_3$ | $Q_1$ | 0 | |
| b 67 | $CH_3$ | $CH_3$ | $N(C_2H_5)_2$ | 0 | |
| b 68 | $CH_3$ | $CH_3$ | $N(n$-Pr$)_2$ | 0 | |
| b 69 | $CH_3$ | $CH_3$ | $N(i$-$C_3H_7)_2$ | 0 | |
| b 70 | $CH_3$ | $CH_3$ | $N(i$-$C_3H_7)CH_2Ph$ | 0 | |
| b 71 | $CH_3$ | $CH_3$ | $N(i$-$C_3H_7)CH_2(4$-Cl—Ph$)$ | 0 | |
| b 72 | $CH_3$ | $CH_3$ | $N(i$-$C_3H_7)Ph$ | 0 | |
| b 73 | $CH_3$ | $CH_3$ | $N(i$-$C_3H_7)(3$-$CH_3$—Ph$)$ | 0 | |
| b 74 | $CH_3$ | $CH_3$ | $N(i$-$C_3H_7)CO_2CH_3$ | 0 | |
| b 75 | $CH_3$ | $CH_3$ | $N(i$-$C_3H_7)CO_2C_2H_5$ | 0 | |
| b 76 | $CH_3$ | $CH_3$ | $N(i$-$C_3H_7)CO_2C_3H_7$-n | 0 | |
| b 77 | $CH_3$ | $CH_3$ | $N(i$-$C_3H_7)CO_2C_3H_7$-i | 0 | |
| b 78 | $CH_3$ | $CH_3$ | $N(i$-$C_3H_7)CO_2C_4H_9$-n | 0 | |
| b 79 | $CH_3$ | $CH_3$ | $N(i$-$C_3H_7)CO_2CH_2CH_2OC_2H_5$ | 0 | |
| b 80 | $CH_3$ | $CH_3$ | $N(i$-$C_3H_7)CO_2CH_2CH_2OPh$ | 0 | |
| b 81 | $CH_3$ | $CH_3$ | $N(i$-$C_3H_7)CO_2(CH_2CH_2O)_2C_4H_9$-n | 0 | |
| b 82 | $CH_3$ | $CH_3$ | $N(i$-$C_3H_7)CH_2CO_2CH_3$ | 0 | |
| b 83 | $CH_3$ | $CH_3$ | $N(i$-$C_3H_7)CH_2CH_2CO_2C_2H_5$ | 0 | |
| b 84 | $CH_3$ | $CH_3$ | $N(n$-$C_4H_9)_2$ | 0 | |
| b 85 | $CH_3$ | $CH_3$ | $N(n$-$C_8H_{17})_2$ | 0 | |
| b 86 | $CH_3$ | $CH_3$ | $N(CH_2Ph)_2$ | 0 | |
| b 87 | $CH_3$ | $CH_3$ | $N(CH_2Ph)CO_2CH_3$ | 0 | |
| b 88 | $CH_3$ | $CH_3$ | $N(CH_2Ph)CO_2C_2H_5$ | 0 | |
| b 89 | $CH_3$ | $CH_3$ | $N(CH_2Ph)CO_2C_3H_7$-n | 0 | |
| b 90 | $CH_3$ | $CH_3$ | $N(CH_2Ph)CO_2C_3H_7$-i | 0 | |
| b 91 | $CH_3$ | $CH_3$ | $N(CH_2Ph)CO_2C_4H_9$-n | 0 | |
| b 92 | $CH_3$ | $CH_3$ | $N(CH_2Ph)CO_2CH_2CH_2OC_2H_5$ | 0 | |
| b 93 | $CH_3$ | $CH_3$ | $N(CH_2Ph)CO_2CH_2CH_2OPh$ | 0 | |
| b 94 | $CH_3$ | $CH_3$ | $N(CH_2Ph)CO_2(CH_2CH_2O)_2C_4H_9$-n | 0 | |
| b 95 | $CH_3$ | $CH_3$ | $N(CH_2Ph)CH_2CO_2CH_3$ | 0 | |
| b 96 | $CH_3$ | $CH_3$ | $N(CH_2Ph)CH_2CH_2CO_2C_2H_5$ | 0 | |
| b 97 | $CH_3$ | $CH_3$ | 1-Pyrrolidinyl | 0 | |
| b 98 | $CH_3$ | $CH_3$ | Piperidino | 0 | |
| b 99 | $CH_3$ | $CH_3$ | Morpholino | 0 | |
| b100 | $CH_3$ | $CH_3$ | $Q_4$ | 0 | |
| b101 | $CH_3$ | $CH_3$ | $Q_2$ | 0 | |
| b102 | $CH_3$ | $CH_3$ | $Q_3$ | 0 | |

TABLE 2-continued (I-b)

$$\text{structure: 1,2,3-thiadiazole with } R^1 \text{ at 4-position and } \text{CON}(R^5)\text{S(O)}_m R^6 \text{ at 5-position}$$

| No. | R¹ | R⁵ | R⁶ | m | Property |
|---|---|---|---|---|---|
| b103 | CH₃ | C₂H₅ | N(CH₃)CO₂C₄H₉-n | 0 | |
| b104 | CH₃ | C₂H₅ | N(i-C₃H₇)CO₂C₄H₉-n | 0 | |
| b105 | CH₃ | C₂H₅ | N(i-C₃H₇)CH₂CH₂CO₂C₂H₅ | 0 | |
| b106 | CH₃ | C₂H₅ | N(n-C₄H₉)₂ | 0 | |
| b107 | CH₃ | C₂H₅ | N(CH₂Ph)CH₂CH₂CO₂C₂H₅ | 0 | |
| b108 | CH₃ | n-C₃H₇ | N(CH₃)CO₂C₄H₉-n | 0 | |
| b109 | CH₃ | n-C₃H₇ | N(i-C₃H₇)CO₂C₄H₉-n | 0 | |
| b110 | CH₃ | n-C₃H₇ | N(i-C₃H₇)CH₂CH₂CO₂C₂H₅ | 0 | |
| b111 | CH₃ | n-C₃H₇ | N(n-C₄H₉)₂ | 0 | |
| b112 | CH₃ | n-C₃H₇ | N(CH₂Ph)CH₂CH₂CO₂C₂H₅ | 0 | |
| b113 | CH₃ | i-C₃H₇ | N(CH₃)CO₂C₄H₉-n | 0 | |
| b114 | CH₃ | i-C₃H₇ | N(i-C₃H₇)CO₂C₄H₉-n | 0 | |
| b115 | CH₃ | i-C₃H₇ | N(i-C₃H₇)CH₂CH₂CO₂C₂H₅ | 0 | |
| b116 | CH₃ | i-C₃H₇ | N(n-C₄H₉)₂ | 0 | |
| b117 | CH₃ | i-C₃H₇ | N(CH₂Ph)CH₂CH₂CO₂C₂H₅ | 0 | |
| b118 | CH₃ | n-C₄H₉ | N(CH₃)CO₂C₄H₉-n | 0 | |
| b119 | CH₃ | n-C₄H₉ | N(i-C₃H₇)CO₂C₄H₉-n | 0 | |
| b120 | CH₃ | n-C₄H₉ | N(i-C₃H₇)CH₂CH₂CO₂C₂H₅ | 0 | |
| b121 | CH₃ | n-C₄H₉ | N(n-C₄H₉)₂ | 0 | |
| b122 | CH₃ | n-C₄H₉ | N(CH₂Ph)CH₂CH₂CO₂C₂H₅ | 0 | |
| b123 | CH₃ | n-C₈H₁₇ | N(CH₃)CO₂C₄H₉-n | 0 | |
| b124 | CH₃ | n-C₈H₁₇ | N(i-C₃H₇)CO₂C₄H₉-n | 0 | |
| b125 | CH₃ | n-C₈H₁₇ | N(i-C₃H₇)CH₂CH₂CO₂C₂H₅ | 0 | |
| b126 | CH₃ | n-C₈H₁₇ | N(n-C₄H₉)₂ | 0 | |
| b127 | CH₃ | n-C₈H₁₇ | N(CH₂Ph)CH₂CH₂CO₂C₂H₅ | 0 | |
| b128 | CH₃ | n-C₁₈H₃₇ | N(CH₃)CO₂C₄H₉-n | 0 | |
| b129 | CH₃ | n-C₁₈H₃₇ | N(i-C₃H₇)CO₂C₄H₉-n | 0 | |
| b130 | CH₃ | n-C₁₈H₃₇ | N(i-C₃H₇)CH₂CH₂CO₂C₂H₅ | 0 | |
| b131 | CH₃ | n-C₁₈H₃₇ | N(n-C₄H₉)₂ | 0 | |
| b132 | CH₃ | n-C₁₈H₃₇ | N(CH₂Ph)CH₂CH₂CO₂C₂H₅ | 0 | |
| b133 | CH₃ | CH₂CH=CH₂ | N(CH₃)CO₂C₄H₉-n | 0 | |
| b134 | CH₃ | CH₂CH=CH₂ | N(i-C₃H₇)CO₂C₄H₉-n | 0 | |
| b135 | CH₃ | CH₂CH=CH₂ | N(i-C₃H₇)CH₂CH₂CO₂C₂H₅ | 0 | |
| b136 | CH₃ | CH₂CH=CH₂ | N(n-C₄H₉)₂ | 0 | |
| b137 | CH₃ | CH₂CH=CH₂ | N(CH₂Ph)CH₂CH₂CO₂C₂H₅ | 0 | |
| b138 | CH₃ | CH₂C≡C—I | N(CH₃)CO₂C₄H₉-n | 0 | |
| b139 | CH₃ | CH₂C≡C—I | N(i-C₃H₇)CO₂C₄H₉-n | 0 | |
| b140 | CH₃ | CH₂C≡C—I | N(i-C₃H₇)CH₂CH₂CO₂C₂H₅ | 0 | |
| b141 | CH₃ | CH₂C≡C—I | N(n-C₄H₉)₂ | 0 | |
| b142 | CH₃ | CH₂C≡C—I | N(CH₂Ph)CH₂CH₂CO₂C₂H₅ | 0 | |
| b143 | CH₃ | c-C₆H₁₁ | N(CH₃)CO₂C₄H₉-n | 0 | |
| b144 | CH₃ | c-C₆H₁₁ | N(i-C₃H₇)CO₂C₄H₉-n | 0 | |
| b145 | CH₃ | c-C₆H₁₁ | N(i-C₃H₇)CH₂CH₂CO₂C₂H₅ | 0 | |
| b146 | CH₃ | c-C₆H₁₁ | N(n-C₄H₉)₂ | 0 | |
| b147 | CH₃ | c-C₆H₁₁ | N(CH₂Ph)CH₂CH₂CO₂C₂H₅ | 0 | |
| b148 | CH₃ | Ph | N(CH₃)CO₂C₄H₉-n | 0 | |
| b149 | CH₃ | Ph | N(i-C₃H₇)CO₂C₄H₉-n | 0 | |
| b150 | CH₃ | Ph | N(i-C₃H₇)CH₂CH₂CO₂C₂H₅ | 0 | |
| b151 | CH₃ | Ph | N(n-C₄H₉)₂ | 0 | |
| b152 | CH₃ | Ph | N(CH₂Ph)CH₂CH₂CO₂C₂H₅ | 0 | |
| b153 | CH₃ | 2-Cl—Ph | N(CH₃)CO₂C₄H₉-n | 0 | |
| b154 | CH₃ | 2-Cl—Ph | N(i-C₃H₇)CO₂C₄H₉-n | 0 | |
| b155 | CH₃ | 2-Cl—Ph | N(i-C₃H₇)CH₂CH₂CO₂C₂H₅ | 0 | |
| b156 | CH₃ | 2-Cl—Ph | N(n-C₄H₉)₂ | 0 | |
| b157 | CH₃ | 2-Cl—Ph | N(CH₂Ph)CH₂CH₂CO₂C₂H₅ | 0 | |
| b158 | CH₃ | 3-Cl—Ph | N(CH₃)CO₂C₄H₉-n | 0 | |
| b159 | CH₃ | 3-Cl—Ph | N(i-C₃H₇)CO₂C₄H₉-n | 0 | |
| b160 | CH₃ | 3-Cl—Ph | N(i-C₃H₇)CH₂CH₂CO₂C₂H₅ | 0 | |
| b161 | CH₃ | 3-Cl—Ph | N(n-C₄H₉)₂ | 0 | |
| b162 | CH₃ | 3-Cl—Ph | N(CH₂Ph)CH₂CH₂CO₂C₂H₅ | 0 | |
| b163 | CH₃ | 4-Cl—Ph | N(CH₃)CO₂C₄H₉-n | 0 | |
| b164 | CH₃ | 4-Cl—Ph | N(i-C₃H₇)CO₂C₄H₉-n | 0 | |
| b165 | CH₃ | 4-Cl—Ph | N(i-C₃H₇)CH₂CH₂CO₂C₂H₅ | 0 | |
| b166 | CH₃ | 4-Cl—Ph | N(n-C₄H₉)₂ | 0 | |
| b167 | CH₃ | 4-Cl—Ph | N(CH₂Ph)CH₂CH₂CO₂C₂H₅ | 0 | |
| b168 | CH₃ | 2-CH₃—Ph | N(CH₃)CO₂C₄H₉-n | 0 | |
| b169 | CH₃ | 2-CH₃—Ph | N(i-C₃H₇)CO₂C₄H₉-n | 0 | |

TABLE 2-continued (I-b)

$$\text{triazole-S-CON(R}^5\text{)-S-(O)}_m\text{R}^6\text{, R}^1\text{ at 4-position}$$

| No. | R¹ | R⁵ | R⁶ | m | Property |
|---|---|---|---|---|---|
| b170 | CH₃ | 2-CH₃—Ph | N(i-C₃H₇)CH₂CH₂CO₂C₂H₅ | 0 | |
| b171 | CH₃ | 2-CH₃—Ph | N(n-C₄H₉)₂ | 0 | |
| b172 | CH₃ | 2-CH₃—Ph | Morpholino | 0 | |
| b173 | CH₃ | 3-CH₃—Ph | N(CH₃)CO₂C₄H₉-n | 0 | |
| b174 | CH₃ | 3-CH₃—Ph | N(i-C₃H₇)CO₂C₄H₉-n | 0 | |
| b175 | CH₃ | 3-CH₃—Ph | N(i-C₃H₇)CH₂CH₂CO₂C₂H₅ | 0 | |
| b176 | CH₃ | 3-CH₃—Ph | N(n-C₄H₉)₂ | 0 | |
| b177 | CH₃ | 3-CH₃—Ph | Morpholino | 0 | |
| b178 | CH₃ | 4-CH₃—Ph | N(CH₃)CO₂C₄H₉-n | 0 | |
| b179 | CH₃ | 4-CH₃—Ph | N(i-C₃H₇)CO₂C₄H₉-n | 0 | |
| b180 | CH₃ | 4-CH₃—Ph | N(i-C₃H₇)CH₂CH₂CO₂C₂H₅ | 0 | |
| b181 | CH₃ | 4-CH₃—Ph | N(n-C₄H₉)₂ | 0 | |
| b182 | CH₃ | 4-CH₃—Ph | N(CH₂Ph)CH₂CH₂CO₂C₂H₅ | 0 | |
| b183 | CH₃ | 4-CH₃—Ph | Morpholino | 0 | m.p. 60° C. (Decomposed) |
| b184 | CH₃ | 4-CH₃—Ph | Q₂ | 0 | m.p. 86° C. (Decomposed) |
| b185 | CH₃ | 3-CF₃—Ph | N(CH₃)CO₂C₄H₉-n | 0 | |
| b186 | CH₃ | 3-CF₃—Ph | N(i-C₃H₇)CO₂C₄H₉-n | 0 | |
| b187 | CH₃ | 3-CF₃—Ph | N(i-C₃H₇)CH₂CH₂CO₂C₂H₅ | 0 | |
| b188 | CH₃ | 3-CF₃—Ph | N(n-C₄H₉)₂ | 0 | |
| b189 | CH₃ | 3-CF₃—Ph | N(CH₂Ph)CH₂CH₂CO₂C₂H₅ | 0 | |
| b190 | CH₃ | 3-CF₃—Ph | Morpholino | 0 | |
| b191 | CH₃ | 3,4-Cl₂—Ph | N(CH₃)CO₂C₄H₉-n | 0 | |
| b192 | CH₃ | 3,4-Cl₂—Ph | N(i-C₃H₇)CO₂C₄H₉-n | 0 | |
| b193 | CH₃ | 3,4-Cl₂—Ph | N(i-C₃H₇)CH₂CH₂CO₂C₂H₅ | 0 | |
| b194 | CH₃ | 3,4-Cl₂—Ph | N(n-C₄H₉)₂ | 0 | |
| b195 | CH₃ | 3,4-Cl₂—Ph | N(CH₂Ph)CH₂CH₂CO₂C₂H₅ | 0 | |
| b196 | CH₃ | 3,5-Cl₂—Ph | N(CH₃)CO₂C₄H₉-n | 0 | |
| b197 | CH₃ | 3,5-Cl₂—Ph | N(i-C₃H₇)CO₂C₄H₉-n | 0 | |
| b198 | CH₃ | 3,5-Cl₂—Ph | N(i-C₃H₇)CH₂CH₂CO₂C₂H₅ | 0 | |
| b199 | CH₃ | 3,5-Cl₂—Ph | N(n-C₄H₉)₂ | 0 | |
| b200 | CH₃ | 3,5-Cl₂—Ph | N(CH₂Ph)CH₂CH₂CO₂C₂H₅ | 0 | |
| b201 | CH₃ | 3,4-(CH₃)₂—Ph | N(CH₃)CO₂C₄H₉-n | 0 | |
| b202 | CH₃ | 3,4-(CH₃)₂—Ph | N(i-C₃H₇)CO₂C₄H₉-n | 0 | |
| b203 | CH₃ | 3,4-(CH₃)₂—Ph | N(i-C₃H₇)CH₂CH₂CO₂C₂H₅ | 0 | |
| b204 | CH₃ | 3,4-(CH₃)₂—Ph | N(n-C₄H₉)₂ | 0 | |
| b205 | CH₃ | 3,4-(CH₃)₂—Ph | N(CH₂Ph)CH₂CH₂CO₂C₂H₅ | 0 | |
| b206 | CH₃ | 3,4-(CH₃)₂—Ph | Morpholino | 0 | |
| b207 | CH₃ | 3-Cl-4-CH₃—Ph | N(CH₃)CO₂C₄H₉-n | 0 | |
| b208 | CH₃ | 3-Cl-4-CH₃—Ph | N(i-C₃H₇)CO₂C₄H₉-n | 0 | |
| b209 | CH₃ | 3-Cl-4-CH₃—Ph | N(i-C₃H₇)CH₂CH₂CO₂C₂H₅ | 0 | |
| b210 | CH₃ | 3-Cl-4-CH₃—Ph | N(n-C₄H₉)₂ | 0 | |
| b211 | CH₃ | 3-Cl-4-CH₃—Ph | N(CH₂Ph)CH₂CH₂CO₂C₂H₅ | 0 | |
| b212 | CH₃ | 3-Cl-4-CH₃—Ph | Morpholino | 0 | |
| b213 | CH₃ | 3-Cl-4-CH₃—Ph | Q₃ | 0 | |
| b214 | CH₃ | 2,4,6-(CH₃)₃—Ph | N(CH₃)CO₂C₄H₉-n | 0 | |
| b215 | CH₃ | 2,4,6-(CH₃)₃—Ph | N(i-C₃H₇)CO₂C₄H₉-n | 0 | |
| b216 | CH₃ | 2,4,6-(CH₃)₃—Ph | N(i-C₃H₇)CH₂CH₂CO₂C₂H₅ | 0 | |
| b217 | CH₃ | 2,4,6-(CH₃)₃—Ph | N(n-C₄H₉)₂ | 0 | |
| b218 | CH₃ | 2,4,6-(CH₃)₃—Ph | N(CH₂Ph)CH₂CH₂CO₂C₂H₅ | 0 | |
| b219 | CH₃ | 3-HO—Ph | N(CH₃)CO₂C₄H₉-n | 0 | |
| b220 | CH₃ | 3-HO—Ph | N(i-C₃H₇)CO₂C₄H₉-n | 0 | |
| b221 | CH₃ | 3-HO—Ph | N(i-C₃H₇)CH₂CH₂CO₂C₂H₅ | 0 | |
| b222 | CH₃ | 3-HO—Ph | N(n-C₄H₉)₂ | 0 | |
| b223 | CH₃ | 3-HO—Ph | N(CH₂Ph)CH₂CH₂CO₂C₂H₅ | 0 | |
| b224 | CH₃ | 2-CH₃O—Ph | N(CH₃)CO₂C₄H₉-n | 0 | |
| b225 | CH₃ | 2-CH₃O—Ph | N(i-C₃H₇)CO₂C₄H₉-n | 0 | |
| b226 | CH₃ | 2-CH₃O—Ph | N(i-C₃H₇)CH₂CH₂CO₂C₂H₅ | 0 | |
| b227 | CH₃ | 2-CH₃O—Ph | N(n-C₄H₉)₂ | 0 | |
| b228 | CH₃ | 2-CH₃O—Ph | N(CH₂Ph)CH₂CH₂CO₂C₂H₅ | 0 | |
| b229 | CH₃ | 4-CF₃O—Ph | N(CH₃)CO₂C₄H₉-n | 0 | |
| b230 | CH₃ | 4-CF₃O—Ph | N(i-C₃H₇)CO₂C₄H₉-n | 0 | |
| b231 | CH₃ | 4-CF₃O—Ph | N(i-C₃H₇)CH₂CH₂CO₂C₂H₅ | 0 | |
| b232 | CH₃ | 4-CF₃O—Ph | N(n-C₄H₉)₂ | 0 | |

TABLE 2-continued (I-b)

$$\underset{R^5}{\overset{N=N}{\underset{S}{\bigvee}}}\overset{R^1}{\underset{CON-S-(O)_mR^6}{\bigvee}}$$

| No. | R¹ | R⁵ | R⁶ | m | Property |
|---|---|---|---|---|---|
| b233 | $CH_3$ | 4-$CF_3$O—Ph | $N(CH_2Ph)CH_2CH_2CO_2C_2H_5$ | 0 | |
| b234 | $CH_3$ | 4-$NO_2$—Ph | $N(CH_3)CO_2C_4H_9$-n | 0 | |
| b235 | $CH_3$ | 4-$NO_2$—Ph | $N(i-C_3H_7)CO_2C_4H_9$-n | 0 | |
| b236 | $CH_3$ | 4-$NO_2$—Ph | $N(i-C_3H_7)CH_2CH_2CO_2C_2H_5$ | 0 | |
| b237 | $CH_3$ | 4-$NO_2$—Ph | $N(n-C_4H_9)_2$ | 0 | |
| b238 | $CH_3$ | 4-$NO_2$—Ph | $N(CH_2Ph)CH_2CH_2CO_2C_2H_5$ | O | |
| b239 | $CH_3$ | 3-CN—Ph | $N(CH_3)CO_2C_4H_9$-n | 0 | |
| b240 | $CH_3$ | 3-CN—Ph | $N(i-C_3H_7)CO_2C_4H_9$-n | 0 | |
| b241 | $CH_3$ | 3-CN—Ph | $N(i-C_3H_7)CH_2CH_2CO_2C_2H_5$ | 0 | |
| b242 | $CH_3$ | 3-CN—Ph | $N(n-C_4H_9)_2$ | 0 | |
| b243 | $CH_3$ | 3-CN—Ph | $N(CH_2Ph)CH_2CH_2CO_2C_2H_5$ | 0 | |
| b244 | $CH_3$ | 2-($CO_2H$)—Ph | $N(CH_3)CO_2C_4H_9$-n | 0 | |
| b245 | $CH_3$ | 2-($CO_2H$)—Ph | $N(i-C_3H_7)CO_2C_4H_9$-n | 0 | |
| b246 | $CH_3$ | 2-($CO_2H$)—Ph | $N(i-C_3H_7)CH_2CH_2CO_2C_2H_5$ | 0 | |
| b247 | $CH_3$ | 2-($CO_2H$)—Ph | $N(n-C_4H_9)_2$ | 0 | |
| b248 | $CH_3$ | 2-($CO_2H$)—Ph | $N(CH_2Ph)CH_2CH_2CO_2C_2H_5$ | 0 | |
| b249 | $CH_3$ | 3-($CO_2H$)—Ph | $N(CH_3)CO_2C_4H_9$-n | 0 | |
| b250 | $CH_3$ | 3-($CO_2H$)—Ph | $N(i-C_3H_7)CO_2C_4H_9$-n | 0 | |
| b251 | $CH_3$ | 3-($CO_2H$)—Ph | $N(i-C_3H_7)CH_2CH_2CO_2C_2H_5$ | 0 | |
| b252 | $CH_3$ | 3-($CO_2H$)—Ph | $N(n-C_4H_9)_2$ | 0 | |
| b253 | $CH_3$ | 3-($CO_2H$)—Ph | $N(CH_2Ph)CH_2CH_2CO_2C_2H_5$ | 0 | |
| b254 | $CH_3$ | 4-($CO_2H$)—Ph | $N(CH_3)CO_2C_4H_9$-n | 0 | |
| b255 | $CH_3$ | 4-($CO_2H$)—Ph | $N(i-C_3H_7)CO_2C_4H_9$-n | 0 | |
| b256 | $CH_3$ | 4-($CO_2H$)—Ph | $N(i-C_3H_7)CH_2CH_2CO_2C_2H_5$ | 0 | |
| b257 | $CH_3$ | 4-($CO_2H$)—Ph | $N(n-C_4H_9)_2$ | 0 | |
| b258 | $CH_3$ | 4-($CO_2H$)—Ph | $N(CH_2Ph)CH_2CH_2CO_2C_2H_5$ | 0 | |
| b259 | $CH_3$ | 2-($CO_2CH_3$)—Ph | $N(CH_3)CO_2C_4H_9$-n | 0 | |
| b260 | $CH_3$ | 2-($CO_2CH_3$)—Ph | $N(i-C_3H_7)CO_2C_4H_9$-n | 0 | |
| b261 | $CH_3$ | 2-($CO_2CH_3$)—Ph | $N(i-C_3H_7)CH_2CH_2CO_2C_2H_5$ | 0 | |
| b262 | $CH_3$ | 2-($CO_2CH_3$)—Ph | $N(n-C_4H_9)_2$ | 0 | |
| b263 | $CH_3$ | 2-($CO_2CH_3$)—Ph | $N(CH_2Ph)CH_2CH_2CO_2C_2H_5$ | 0 | |
| b264 | $CH_3$ | 4-($CO_2CH_3$)—Ph | $N(CH_3)CO_2C_4H_9$-n | 0 | |
| b265 | $CH_3$ | 4-($CO_2CH_3$)—Ph | $N(i-C_3H_7)CO_2C_4H_9$-n | 0 | |
| b266 | $CH_3$ | 4-($CO_2CH_3$)—Ph | $N(i-C_3H_7)CH_2CH_2CO_2C_2H_5$ | 0 | |
| b267 | $CH_3$ | 4-($CO_2CH_3$)—Ph | $N(n-C_4H_9)_2$ | 0 | |
| b268 | $CH_3$ | 4-($CO_2CH_3$)—Ph | $N(CH_2Ph)CH_2CH_2CO_2C_2H_5$ | 0 | |
| b269 | $CH_3$ | 4-($CONHCH_3$)—Ph | $N(CH_3)CO_2C_4H_9$-n | 0 | |
| b270 | $CH_3$ | 4-($CONHCH_3$)—Ph | $N(i-C_3H_7)CO_2C_4H_9$-n | 0 | |
| b271 | $CH_3$ | 4-($CONHCH_3$)—Ph | $N(i-C_3H_7)CH_2CH_2CO_2C_2H_5$ | 0 | |
| b272 | $CH_3$ | 4-($CONHCH_3$)—Ph | $N(n-C_4H_9)_2$ | 0 | |
| b273 | $CH_3$ | 4-($CONHCH_3$)—Ph | $N(CH_2Ph)CH_2CH_2CO_2C_2H_5$ | 0 | |
| b274 | $CH_3$ | $CH_2Ph$ | $N(CH_3)CO_2C_4H_9$-n | 0 | |
| b275 | $CH_3$ | $CH_2Ph$ | $N(i-C_3H_7)CO_2C_4H_9$-n | 0 | |
| b276 | $CH_3$ | $CH_2Ph$ | $N(i-C_3H_7)CH_2CH_2CO_2C_2H_5$ | 0 | |
| b277 | $CH_3$ | $CH_2Ph$ | $N(n-C_4H_9)_2$ | 0 | |
| b278 | $CH_3$ | $CH_2Ph$ | $N(CH_2Ph)CH_2CH_2CO_2C_2H_5$ | 0 | |
| b279 | $C_2H_5$ | $CH_3$ | $N(CH_3)CO_2C_4H_9$-n | 0 | |
| b280 | $C_2H_5$ | $CH_3$ | $N(i-C_3H_7)CO_2C_4H_9$-n | 0 | |
| b281 | $C_2H_5$ | $CH_3$ | $N(i-C_3H_7)CH_2CH_2CO_2C_2H_5$ | 0 | |
| b282 | $C_2H_5$ | $CH_3$ | $N(n-C_4H_9)_2$ | 0 | |
| b283 | $C_2H_5$ | $CH_3$ | $N(CH_2Ph)CH_2CH_2CO_2C_2H_5$ | 0 | |
| b284 | i-$C_3H_7$ | $CH_3$ | $CH_3$ | 0 | |
| b285 | i-$C_3H_7$ | $CH_3$ | i-$C_3H_7$ | 0 | |
| b286 | i-$C_3H_7$ | $CH_3$ | n-$C_6H_{13}$ | 0 | |
| b287 | i-$C_3H_7$ | $CH_3$ | $CH_2CH_2Br$ | 0 | |
| b288 | i-$C_3H_7$ | $CH_3$ | $CH_2CH_2CH_2I$ | 0 | |
| b289 | i-$C_3H_7$ | $CH_3$ | Ph | 0 | |
| b290 | i-$C_3H_7$ | $CH_3$ | 4-Cl—Ph | 0 | |
| b291 | i-$C_3H_7$ | $CH_3$ | 2,4-$Cl_2$—Ph | 0 | |
| b292 | i-$C_3H_7$ | $CH_3$ | 2-$CH_3$—Ph | 0 | |
| b293 | i-$C_3H_7$ | $CH_3$ | $CH_2Ph$ | 0 | |
| b294 | i-$C_3H_7$ | $CH_3$ | $N(CH_3)_2$ | 0 | |
| b295 | i-$C_3H_7$ | $CH_3$ | $N(CH_3)C_2H_5$ | 0 | |
| b296 | i-$C_3H_7$ | $CH_3$ | $N(CH_3)C_3H_7$-n | 0 | |
| b297 | i-$C_3H_7$ | $CH_3$ | $N(CH_3)C_3H_7$-i | 0 | |
| b298 | i-$C_3H_7$ | $CH_3$ | $N(CH_3)C_4H_9$-n | 0 | |
| b299 | i-$C_3H_7$ | $CH_3$ | $N(CH_3)C_8H_{17}$-n | 0 | |

TABLE 2-continued (I-b)

$$\text{triazole-S-CON(R}^5\text{)-S-(O)}_m\text{R}^6$$ with $R^1$ on ring

| No. | $R^1$ | $R^5$ | $R^6$ | m | Property |
|---|---|---|---|---|---|
| b300 | i-$C_3H_7$ | $CH_3$ | $N(CH_3)CH_2Ph$ | 0 | |
| b301 | i-$C_3H_7$ | $CH_3$ | $N(CH_3)CH_2(4\text{-Cl}\text{—Ph})$ | 0 | |
| b302 | i-$C_3H_7$ | $CH_3$ | $N(CH_3)Ph$ | 0 | |
| b303 | i-$C_3H_7$ | $CH_3$ | $N(CH_3)(3\text{-CH}_3\text{—Ph})$ | 0 | |
| b304 | i-$C_3H_7$ | $CH_3$ | $N(CH_3)CO_2CH_3$ | 0 | |
| b305 | i-$C_3H_7$ | $CH_3$ | $N(CH_3)CO_2C_2H_5$ | 0 | |
| b306 | i-$C_3H_7$ | $CH_3$ | $N(CH_3)CO_2C_3H_7\text{-n}$ | 0 | |
| b307 | i-$C_3H_7$ | $CH_3$ | $N(CH_3)CO_2C_3H_7\text{-i}$ | 0 | |
| b308 | i-$C_3H_7$ | $CH_3$ | $N(CH_3)CO_2C_4H_9\text{-n}$ | 0 | |
| b309 | i-$C_3H_7$ | $CH_3$ | $N(CH_3)CO_2CH_2CH_2OC_2H_5$ | 0 | |
| b310 | i-$C_3H_7$ | $CH_3$ | $N(CH_3)CO_2CH_2CH_2OPh$ | 0 | |
| b311 | i-$C_3H_7$ | $CH_3$ | $N(CH_3)CO_2(CH_2CH_2O)_2C_4H_9\text{-n}$ | 0 | |
| b312 | i-$C_3H_7$ | $CH_3$ | $N(CH_3)CH_2CO_2CH_3$ | 0 | |
| b313 | i-$C_3H_7$ | $CH_3$ | $N(CH_3)CH_2CH_2CO_2C_2H_5$ | 0 | |
| b314 | i-$C_3H_7$ | $CH_3$ | $N(CH_3)COPh$ | 0 | |
| b315 | i-$C_3H_7$ | $CH_3$ | $Q_1$ | 0 | |
| b316 | i-$C_3H_7$ | $CH_3$ | $N(C_2H_5)_2$ | 0 | |
| b317 | i-$C_3H_7$ | $CH_3$ | $N(n\text{-}C_3H_7)_2$ | 0 | |
| b318 | i-$C_3H_7$ | $CH_3$ | $N(i\text{-}C_3H_7)_2$ | 0 | |
| b319 | i-$C_3H_7$ | $CH_3$ | $N(n\text{-}C_3H_7)CH_2Ph$ | 0 | |
| b320 | i-$C_3H_7$ | $CH_3$ | $N(n\text{-}C_3H_7)CH_2(4\text{-Cl}\text{—Ph})$ | 0 | |
| b321 | i-$C_3H_7$ | $CH_3$ | $N(n\text{-}C_3H_7)Ph$ | 0 | |
| b322 | i-$C_3H_7$ | $CH_3$ | $N(n\text{-}C_3H_7)(3\text{-CH}_3\text{—Ph})$ | 0 | |
| b323 | i-$C_3H_7$ | $CH_3$ | $N(n\text{-}C_3H_7)CO_2CH_3$ | 0 | |
| b324 | i-$C_3H_7$ | $CH_3$ | $N(n\text{-}C_3H_7)CO_2C_2H_5$ | 0 | |
| b325 | i-$C_3H_7$ | $CH_3$ | $N(n\text{-}C_3H_7)CO_2C_3H_7\text{-n}$ | 0 | |
| b326 | i-$C_3H_7$ | $CH_3$ | $N(n\text{-}C_3H_7)CO_2C_3H_7\text{-i}$ | 0 | |
| b327 | i-$C_3H_7$ | $CH_3$ | $N(n\text{-}C_3H_7)CO_2C_4H_9\text{-n}$ | 0 | |
| b328 | i-$C_3H_7$ | $CH_3$ | $N(n\text{-}C_3H_7)CO_2CH_2CH_2OC_2H_5$ | 0 | |
| b329 | i-$C_3H_7$ | $CH_3$ | $N(n\text{-}C_3H_7)CO_2CH_2CH_2OPh$ | 0 | |
| b330 | i-$C_3H_7$ | $CH_3$ | $N(n\text{-}C_3H_7)CO_2(CH_2CH_2O)_2C_4H_9\text{-n}$ | 0 | |
| b331 | i-$C_3H_7$ | $CH_3$ | $N(i\text{-}C_3H_7)CH_2CO_2CH_3$ | 0 | |
| b332 | i-$C_3H_7$ | $CH_3$ | $N(i\text{-}C_3H_7)CH_2CH_2CO_2C_2H_5$ | 0 | |
| b333 | i-$C_3H_7$ | $CH_3$ | $N(n\text{-}C_4H_9)_2$ | 0 | |
| b334 | i-$C_3H_7$ | $CH_3$ | $N(n\text{-}C_8H_{17})_2$ | 0 | |
| b335 | i-$C_3H_7$ | $CH_3$ | $N(CH_2Ph)_2$ | 0 | |
| b336 | i-$C_3H_7$ | $CH_3$ | $N(CH_2Ph)CO_2CH_3$ | 0 | |
| b337 | i-$C_3H_7$ | $CH_3$ | $N(CH_2Ph)CO_2C_2H_5$ | 0 | |
| b338 | i-$C_3H_7$ | $CH_3$ | $N(CH_2Ph)CO_2C_3H_7\text{-n}$ | 0 | |
| b339 | i-$C_3H_7$ | $CH_3$ | $N(CH_2Ph)CO_2C_3H_7\text{-i}$ | 0 | |
| b340 | i-$C_3H_7$ | $CH_3$ | $N(CH_2Ph)CO_2C_4H_9\text{-n}$ | 0 | |
| b341 | i-$C_3H_7$ | $CH_3$ | $N(CH_2Ph)CO_2CH_2CH_2OC_2H_5$ | 0 | |
| b342 | i-$C_3H_7$ | $CH_3$ | $N(CH_2Ph)CO_2CH_2CH_2OPh$ | 0 | |
| b343 | i-$C_3H_7$ | $CH_3$ | $N(CH_2Ph)CO_2(CH_2CH_2O)_2C_4H_9\text{-n}$ | 0 | |
| b344 | i-$C_3H_7$ | $CH_3$ | $N(CH_2Ph)CH_2CO_2CH_3$ | 0 | |
| b345 | i-$C_3H_7$ | $CH_3$ | $N(CH_2Ph)CH_2CH_2CO_2C_2H_5$ | 0 | |
| b346 | i-$C_3H_7$ | $CH_3$ | 1-Pyrrolidinyl | 0 | |
| b347 | i-$C_3H_7$ | $CH_3$ | Piperidino | 0 | |
| b348 | i-$C_3H_7$ | $CH_3$ | Morpholino | 0 | |
| b349 | i-$C_3H_7$ | $CH_3$ | $Q_4$ | 0 | |
| b350 | i-$C_3H_7$ | $CH_3$ | $Q_2$ | 0 | |
| b351 | i-$C_3H_7$ | $CH_3$ | $Q_3$ | 0 | |
| b352 | i-$C_3H_7$ | n-$C_8H_{17}$ | $N(CH_3)CO_2C_4H_9\text{-n}$ | 0 | |
| b353 | i-$C_3H_7$ | n-$C_8H_{17}$ | $N(i\text{-}C_3H_7)CO_2C_4H_9\text{-n}$ | 0 | |
| b354 | i-$C_3H_7$ | n-$C_8H_{17}$ | $N(i\text{-}C_3H_7)CH_2CH_2CO_2C_2H_5$ | 0 | |
| b355 | i-$C_3H_7$ | n-$C_8H_{17}$ | $N(n\text{-}C_4H_9)_2$ | 0 | |
| b356 | i-$C_3H_7$ | n-$C_8H_{17}$ | $N(CH_2Ph)CH_2CH_2CO_2C_2H_5$ | 0 | |
| b357 | i-$C_3H_7$ | 4-Cl—Ph | $N(CH_3)CO_2C_4H_9\text{-n}$ | 0 | |
| b358 | i-$C_3H_7$ | 4-Cl—Ph | $N(i\text{-}C_3H_7)CO_2C_4H_9\text{-n}$ | 0 | |
| b359 | i-$C_3H_7$ | 4-Cl—Ph | $N(i\text{-}C_3H_7)CH_2CH_2CO_2C_2H_5$ | 0 | |
| b360 | i-$C_3H_7$ | 4-Cl—Ph | $N(n\text{-}C_4H_9)_2$ | 0 | |
| b361 | i-$C_3H_7$ | 4-Cl—Ph | $N(CH_2Ph)CH_2CH_2CO_2C_2H_5$ | 0 | |
| b362 | i-$C_3H_7$ | 2-$CH_3$—Ph | $N(CH_3)CO_2C_4H_9\text{-n}$ | 0 | |
| b363 | i-$C_3H_7$ | 2-$CH_3$—Ph | $N(i\text{-}C_3H_7)CO_2C_4H_9\text{-n}$ | 0 | |
| b364 | i-$C_3H_7$ | 2-$CH_3$—Ph | $N(i\text{-}C_3H_7)CH_2CH_2CO_2C_2H_5$ | 0 | |
| b365 | i-$C_3H_7$ | 2-$CH_3$—Ph | $N(n\text{-}C_4H_9)_2$ | 0 | |
| b366 | i-$C_3H_7$ | 2-$CH_3$—Ph | $N(CH_2Ph)CH_2CH_2CO_2C_2H_5$ | 0 | |

TABLE 2-continued (I-b)

Structure: 1,2,3-thiadiazole with R¹ at 4-position and CON(R⁵)—S(O)ₘR⁶ at 5-position

| No. | R¹ | R⁵ | R⁶ | m | Property |
|---|---|---|---|---|---|
| b367 | i-C₃H₇ | 4-CF₃O—Ph | N(CH₃)CO₂C₄H₉-n | 0 | |
| b368 | i-C₃H₇ | 4-CF₃O—Ph | N(i-C₃H₇)CO₂C₄H₉-n | 0 | |
| b369 | i-C₃H₇ | 4-CF₃O—Ph | N(i-C₃H₇)CH₂CH₂CO₂C₂H₅ | 0 | |
| b370 | i-C₃H₇ | 4-CF₃O—Ph | N(n-C₄H₉)₂ | 0 | |
| b371 | i-C₃H₇ | 4-CF₃O—Ph | N(CH₂Ph)CH₂CH₂CO₂C₂H₅ | 0 | |
| b372 | n-C₄H₉ | CH₃ | N(CH₃)CO2C₄H₉-n | 0 | |
| b373 | n-C₄H₉ | CH₃ | N(i-C₃H₇)CO₂C₄H₉-n | 0 | |
| b374 | n-C₄H₉ | CH₃ | N(i-C₃H₇)CH₂CH₂CO₂C₂H₅ | 0 | |
| b375 | n-C₄H₉ | CH₃ | N(n-C₄H₉)₂ | 0 | |
| b376 | n-C₄H₉ | CH₃ | N(CH₂Ph)CH₂CH₂CO₂C₂H₅ | 0 | |
| b377 | n-C₆H₁₃ | CH₃ | N(CH₃)CO₂C₄H₉-n | 0 | |
| b378 | n-C₆H₁₃ | CH₃ | N(i-C₃H₇)CO₂C₄H₉-n | 0 | |
| b379 | n-C₆H₁₃ | CH₃ | N(i-C₃H₇)CH₂CH₂CO₂C₂H₅ | 0 | |
| b380 | n-C₆H₁₃ | CH₃ | N(n-C₄H₉)₂ | 0 | |
| b381 | n-C₆H₁₃ | CH₃ | N(CH₂Ph)CH₂CH₂CO₂C₂H₅ | 0 | |
| b382 | c-C₃H₅ | CH₃ | N(CH₃)CO2C₄H₉-n | 0 | |
| b381 | c-C₃H₅ | CH₃ | N(CH₂Ph)CH₂CH₂CO₂C₂H₅ | 0 | |
| b382 | c-C₃H₅ | CH₃ | N(CH₃)CO₂C₄H₉-n | 0 | |
| b383 | c-C₃H₅ | CH₃ | N(i-C₃H₇)CO₂C₄H₉-n | 0 | |
| b384 | c-C₃H₅ | CH₃ | N(i-C₃H₇)CH₂CH₂CO₂C₂H₅ | 0 | |
| b385 | c-C₃H₅ | CH₃ | N(n-C₄H₉)₂ | 0 | |
| b386 | c-C₃H₅ | CH₃ | N(CH₂Ph)CH₂CH₂CO₂C₂H₅ | 0 | |
| b387 | c-C₆H₁₁ | CH₃ | N(CH₃)CO₂C₄H₉-n | 0 | |
| b388 | c-C₆H₁₁ | CH₃ | N(i-C₃H₇)CO₂C₄H₉-n | 0 | |
| b389 | c-C₆H₁₁ | CH₃ | N(i-C₃H₇)CH₂CH₂CO₂C₂H₅ | 0 | |
| b390 | c-C₆H₁₁ | CH₃ | N(n-C₄H₉)₂ | 0 | |
| b391 | c-C₆H₁₁ | CH₃ | N(CH₂Ph)CH₂CH₂CO₂C₂H₅ | 0 | |
| b392 | H | H | CH₃ | 1 | |
| b393 | H | H | i-C₃H₇ | 1 | |
| b394 | H | H | Ph | 1 | |
| b395 | H | H | CH₂Ph | 1 | |
| b396 | H | H | N(CH₃)₂ | 1 | |
| b397 | H | H | CH₃ | 2 | |
| b398 | H | H | i-C₃H₇ | 2 | |
| b399 | H | H | Ph | 2 | |
| b400 | H | H | CH₂Ph | 2 | |
| b401 | H | H | N(CH₃)₂ | 2 | |
| b402 | H | H | N(n-C₄H₉)₂ | 2 | |
| b403 | H | H | Morpholino | 2 | |
| b404 | H | CH₃ | CH₃ | 2 | |
| b405 | H | CH₃ | i-C₃H₇ | 2 | |
| b406 | H | CH₃ | Ph | 2 | |
| b407 | H | CH₃ | CH₂Ph | 2 | |
| b408 | CH₃ | H | CH₃ | 2 | m.p. 165° C. |
| b409 | CH₃ | H | C₂H₅ | 2 | |
| b410 | CH₃ | H | n-C₃H₇ | 2 | |
| b411 | CH₃ | H | i-C₃H₇ | 2 | |
| b412 | CH₃ | H | n-C₄H₉ | 2 | |
| b413 | CH₃ | H | i-C₄H₉ | 2 | |
| b414 | CH₃ | H | sec-C₄H₉ | 2 | |
| b415 | CH₃ | H | t-C₄H₉ | 2 | |
| b416 | CH₃ | H | c-C₆H₁₁ | 2 | |
| b417 | CH₃ | H | n-C₈H₁₇ | 2 | |
| b418 | CH₃ | H | n-C₁₆H₃₃ | 2 | |
| b419 | CH₃ | H | CH₂Cl | 2 | |
| b420 | CH₃ | H | CF₃ | 2 | |
| b421 | CH₃ | H | CH₂CH₂F | 2 | |
| b422 | CH₃ | H | CH₂CF₃ | 2 | |
| b423 | CH₃ | H | CH₂CH₂F | 2 | |
| b424 | CH₃ | H | CH₂CH₂Cl | 2 | |
| b425 | CH₃ | H | CH₂CH₂Br | 2 | |
| b426 | CH₃ | H | (CF₂)₃CF₃ | 2 | |
| b427 | CH₃ | H | (CF₂)₇CF₃ | 2 | |
| b428 | CH₃ | H | CH₂CH=CH₂ | 2 | |
| b429 | CH₃ | H | CH₂CH=CHCl | 2 | |
| b430 | CH₃ | H | CH₂C≡CH | 2 | |
| b431 | CH₃ | H | 2-Cyclohexenyl | 2 | |

TABLE 2-continued (I-b)

| No. | R¹ | R⁵ | R⁶ | m | Property |
|---|---|---|---|---|---|
| b432 | CH₃ | H | 4-F—Ph | 2 | |
| b433 | CH₃ | H | 2-Cl—Ph | 2 | |
| b434 | CH₃ | H | 3-Cl—Ph | 2 | |
| b435 | CH₃ | H | 4-Cl—Ph | 2 | m.p. 187° C. |
| b436 | CH₃ | H | 4-Br—Ph | 2 | |
| b437 | CH₃ | H | 4-I—Ph | 2 | |
| b438 | CH₃ | H | 2,4-Cl₂—Ph | 2 | |
| b439 | CH₃ | H | 3,5-Cl₂—Ph | 2 | |
| b440 | CH₃ | H | 2-CH₃—Ph | 2 | |
| b441 | CH₃ | H | 3-CH₃—Ph | 2 | |
| b442 | CH₃ | H | 4-CH₃—Ph | 2 | |
| b443 | CH₃ | H | 4-C₂H₅—Ph | 2 | |
| b444 | CH₃ | H | 4-t-C₄H₉—Ph | 2 | |
| b445 | CH₃ | H | 2-Furyl | 2 | |
| b446 | CH₃ | H | 2-Thienyl | 2 | |
| b447 | CH₃ | H | 3-Pyridyl | 2 | |
| b448 | CH₃ | H | 6-Cl-3-Pyridyl | 2 | |
| b449 | CH₃ | H | CH₂Ph | 2 | |
| b450 | CH₃ | H | CH₂(4-Cl—Ph) | 2 | |
| b451 | CH₃ | H | CH₂(4-CH₃—Ph) | 2 | |
| b452 | CH₃ | H | N(CH₃)₂ | 2 | |
| b453 | CH₃ | CH₃ | CH₃ | 2 | |
| b454 | CH₃ | CH₃ | Ph | 2 | |
| b455 | CH₃ | CH₃ | CH₂Ph | 2 | |
| b456 | CH₃ | CH₃ | N(CH₃)₂ | 2 | |
| b457 | CH₃ | CH₃ | N(CH₃)CO₂CH₃ | 2 | |
| b458 | CH₃ | CH₃ | N(CH₃)CO₂C₄H₉-n | 2 | |
| b459 | CH₃ | CH₃ | N(C₂H₅)₂ | 2 | |
| b460 | CH₃ | CH₃ | N(i-C₃H₇)₂ | 2 | |
| b461 | CH₃ | CH₃ | N(i-C₃H₇)₂ | 2 | |
| b462 | CH₃ | CH₃ | N(i-C₃H₇)CO₂CH₃ | 2 | |
| b463 | CH₃ | CH₃ | N(i-C₃H₇)CO₂C₄H₉-n | 2 | |
| b464 | CH₃ | CH₃ | N(i-C₃H₇)CH₂CH₂CO₂C₂H₅ | 2 | |
| b465 | CH₃ | CH₃ | N(n-C₄H₉)₂ | 2 | |
| b466 | CH₃ | CH₃ | N(CH₂Ph)CH₂CH₂CO₂C₂H₅ | 2 | |
| b467 | CH₃ | CH₃ | Morpholino | 2 | |
| b468 | CH₃ | i-C₃H₇ | CH₃ | 2 | |
| b469 | CH₃ | i-C₃H₇ | Ph | 2 | |
| b470 | CH₃ | i-C₃H₇ | CH₂Ph | 2 | |
| b471 | CH₃ | Ph | CH₃ | 2 | |
| b472 | CH₃ | Ph | Ph | 2 | |
| b473 | CH₃ | Ph | CH₂Ph | 2 | |
| b474 | C₂H₅ | H | CH₃ | 2 | |
| b475 | C₂H₅ | H | i-C₃H₇ | 2 | |
| b476 | C₂H₅ | H | Ph | 2 | |
| b477 | C₂H₅ | H | CH₂Ph | 2 | |
| b478 | i-C₃H₇ | H | CH₃ | 2 | |
| b479 | i-C₃H₇ | H | i-C₃H₇ | 2 | |
| b480 | i-C₃H₇ | H | Ph | 2 | |
| b481 | i-C₃H₇ | H | CH₂Ph | 2 | |
| b482 | n-C₄H₉ | H | CH₃ | 2 | |
| b483 | n-C₄H₉ | H | i-C₃H₇ | 2 | |
| b484 | n-C₄H₉ | H | Ph | 2 | |
| b485 | n-C₄H₉ | H | CH₂Ph | 2 | |
| b486 | c-C₃H₅ | H | CH₃ | 2 | |
| b487 | c-C₃H₅ | H | i-C₃H₇ | 2 | |
| b488 | c-C₃H₅ | H | Ph | 2 | |
| b489 | c-C₃H₅ | H | CH₂Ph | 2 | |

In Table 2, "Ph" represents a phenyl group, "c-" represents an alicyclic hydrocarbon group, and $Q_1$, $Q_2$, $Q_3$ and $Q_4$ represent the following substituents:

$Q_1$:

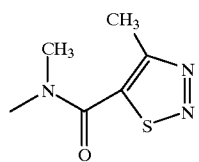

$Q_2$:

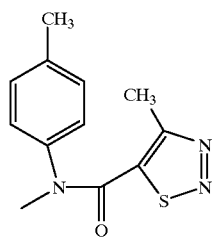

$Q_3$:

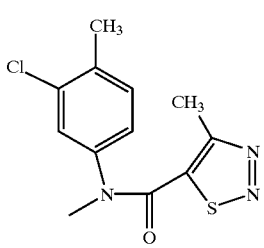

$Q_4$:

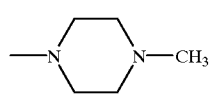

Morpholino:

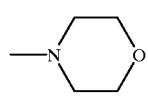

2-Cyclohexenyl:

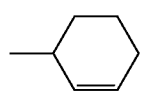

1-Pyrrolidinyl:

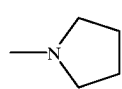

Piperidino:

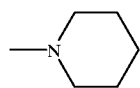

The 1,2,3-thiadiazole derivatives represented by general formula (I) are useful as a plant disease controller, and they exhibit a very high controlling effect against various diseases. Specific examples of the diseases against which the compounds of the present invention exhibit a marked effect include rice blast (*Pyricularia oryzae*), rice sheath blight (*Rhizoctonia solani*), rice helminthosporium leaf spot (*Cochiobolus miyabeanus*), powdery mildew of various host plants such as powdery mildew of barley and wheat (*Erysiphe graminis*), oats crown rust (*Puccinia coronata*), stem rust of other plants, late blight of tomato (*Phytophthora infestans*), late blight of other plants, late blight or Phytophthora rots of various plants such as cucumber downy mildew (*Pseudoperonospora cubensis*), grape downy mildew (*Plasmopara viticola*), etc., apple scab (*Venturia inaequalis*), apple alternaria leaf spot (*Alternaria mali*), pear black spot (*Alternaria kikuchiana*), citrus melanose (*Diaporthe citri*), bacterial diseases due to Genus Pseudomonas such as cucumber bacterial blight (*Pseudomonas syringae* pv. *lachrymans*) and tomato bacterial wilt (*Pseudomonas solanacearum*), bacterial diseases due to Genus Xanthomonas such as cabbage black rot (*Xanthomonas campestris*), rice bacterial leaf blight (*Xanthomonas oryzae*) and citrus canker (*Xanthomonas citri*), and bacterial diseases due to Genus Erwinia such as cabbage bacterial soft rot (*Erwinia carotovora*), and viral diseases such as tobacco mosaic (*tobacco mosaic* virus), etc.

The plant disease controller of the present invention containing the 1,2,3-thiadiazole derivative represented by general formula (I) as an active ingredient exhibits a marked controlling effect against the above-mentioned diseases injuring the crop plants of paddy field, crop plants of upland field, fruit plants, vegetables, and other crop plants and flower plants. Therefore, the desired effects of the agrohorticultural disease controller of the present invention can be obtained by applying the disease controller to paddy field water, stalks and leaves or soil of the paddy field, upland field, fruit trees, vegetables, other crops, flowers and ornamental plants at a season at which the diseases are expected to occur, before their occurrence or at the time when their occurrence is confirmed.

In general, the plant disease controller of the present invention is used after being prepared into a conventionally usable form according to an ordinary manner for preparation of agrochemicals.

That is, the 1,2,3-thiadiazole derivative of the present invention represented by general formula (I) and, optionally, an adjuvant are blended with a suitable inert carrier in a proper proportion and prepared into a suitable preparation form such as suspension, emulsion, solution, wettable powder, granule, dust, tablet or the like through dissolution, separation, dispersion, mixing, impregnation, adsorption or adhesion.

The inert carrier used in the present invention may be either solid or liquid. As the solid carrier material, there can be referred to soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, acid clay, etc.), talcs (e.g. talc, pyrophyllite, etc.), silica materials (e.g. diatomaceous earth, silica sand, mica, white carbon, i.e. synthetic high-dispersion silicic acid, also called finely divided hydrated silica or hydrated silicic acid, some of the commercially available products thereof contain calcium silicate as the major component), activated carbon, powdered sulfur, pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea, ammonium chloride, etc.), and compost. These solid carriers may be used alone or as a mixture thereof.

The liquid carrier material is selected from those which have solubility in themselves or those which have no solubility in themselves but are capable of dispersing an active ingredient by the aid of an adjuvant. The following are typical examples of the liquid carrier, which can be used alone or as a mixture thereof. Water; alcohols such as methanol, ethanol, isopropanol, butanol, ethylene glycol and the like; ketones such as acetone, methyl ethyl ketone, methyl isobutyl ketone, diisobutyl ketone, cyclohexanone and the like; ethers such as ethyl ether, dioxane, cellosolve, dipropyl ether, tetrahydrofuran and the like; aliphatic hydrocarbons such as kerosene, mineral oils and the like, aromatic hydrocarbons such as benzene, toluene, xylene, solvent naphtha, alkylnaphthalene and the like; halogenated hydrocarbons such as dichlorethane, chloroform, carbon tetrachloride, chlorobenzenes and the like; esters such as ethyl acetate, diisopropyl phthalate, dibutyl phthalate, dioctyl phthalate and the like; amides such as dimethylformamide, diethylformamide, dimethylacetamide and the like; nitriles such as acetonitrile and the like; dimethyl sulfoxide; etc.

The following are typical examples of other adjuvants, which are used depending on purpose and may be used alone or in combination in some cases or not used at all.

For the purpose of emulsifying, dispersing, solubilizing and/or wetting an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensates, ligninsulfonates, higher alcohol sulfuric ester salts, etc.

Further, for the purpose of stabilizing, tackifying and/or binding a dispersion of an active ingredient, there may be used an adjuvant such as casein, gelatin, starch, methyl cellulose, carboxymethyl cellulose, gum arabic, polyvinyl alcohol, turpentine oil, bran oil, bentonite, ligninsulfonate and the like.

For the purpose of improving flowability of a solid product, adjuvants such as wax, stearic acid salts, alkyl esters of phosphoric acid, etc.

Adjuvants such as naphthalenesulfonic acid condensates, polycondensates of phosphates, etc. may be used as a peptizer for dispersible products.

Adjuvants such as silicon oils may also be used as a defoaming agent.

The content of active ingredient may be varied in accordance with need. For example, in dusts and granules, the suitable content thereof is from 0.01 to 50% by weight. In emulsifiable concentrate and wettable powder, too, an active ingredient content of from 0.01 to 50% by weight is suitable.

The plant disease controller of the present invention is used to control various diseases by applying its effective amount for the disease control either as it is or in the form of dilution or suspension in an appropriate quantity of water or the like, to a crop on which occurrence of the diseases is expected or to a site where the occurrence of the diseases is undesirable. For example, in order to control the diseases of paddy rice, said disease controller can be used by the method of submerged application to a regular paddy field, application to a rice nursery bed, dressing of seeds for direct sowing on flooded paddy field, or seed disinfection. For the purpose of controlling the diseases of wheat and barley, the plant disease controller of the present invention may be sprayed to stalks or leaves, or applied to the soil aiming at absorption from the roots.

The applying dosage of the plant disease controller of the present invention may vary depending on various factors such as purpose, disease to be controlled, growth state of crop, tendency of occurrence of the disease, weather, environmental conditions, preparation form, method of application, site of application, and time of application. However, it may be properly chosen in the range of 0.1 gram to 10 kilograms, in terms of active ingredient, per 10 areas depending upon purposes.

It is also possible to use the plant disease controller of the present invention in admixture with other plant disease controllers in order to expand spectrum of controllable diseases and the period of time when an effective application is possible, or to reduce the dosage.

Typical examples, recipe examples and test examples of the 1,2,3-thiadiazole derivatives represented by general formula (I) are shown below. The present invention is by no means limited by these examples.

EXAMPLE 1-1

Production of 2-(4-methyl-1,2,3-thiadiazol-5-yl-carbonylamino)benzoic acid

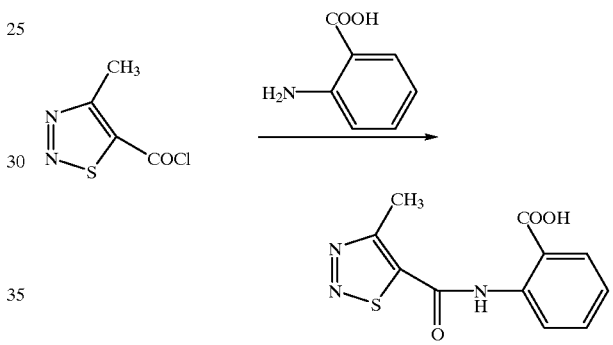

In 50 ml of water were dissolved 1.2 g (31 mmol) of sodium hydroxide and 4.2 g (31 mmol) of anthranilic acid. While cooling the solution with ice, 5 g (31 mmol) of 4-methyl-1,2,3-thiadiazole-5-carboxylic acid chloride was dropwise added thereto over a period of 30 minutes. After the dropping, the resulting mixture was reacted with stirring at room temperature for 30 minutes. After the reaction was completed, the crystalline product deposited from the reaction mixture was collected by filtration and washed with methanol and ethyl acetate. Thus, 7.1 g of the objective compound was obtained.

Property: m.p. 223° C.; Yield: 87%.

EXAMPLE 1-2

Production of 2-(4-methyl-1,2,3-thiadiazol-5-yl)-4H-4-oxo-3,1-benzoxazine (Compound No. a27)

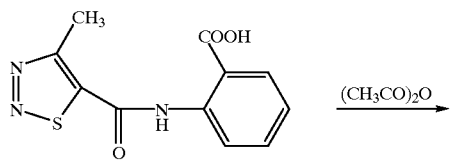

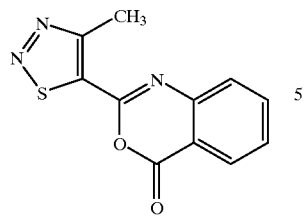

To 5 g (19 mmol) of the 2-(4-methyl-1,2,3-thiadiazol-5-yl-carbonylamino)benzoic acid obtained in 1-1 was added 50 ml of acetic anhydride. The resulting mixture was reacted with heating under reflux for 2 hours. After the reaction was completed, the reaction mixture was cooled to room temperature, and the resulting crystalline product was collected by filtration and washed with methanol and ethyl acetate. Thus, 4 g of the objective compound was obtained.

Property: m.p. 161° C.; Yield: 86%.

EXAMPLE 2

Production of 2-(4-methyl-1,2,3-thiadiazol-5-yl)-4H-4-oxo-3,1-benzoxazine (Compound No. a27)

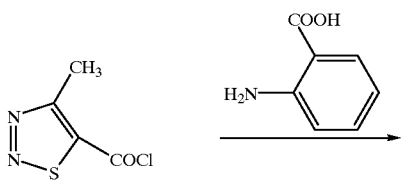

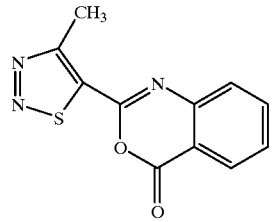

In 30 ml of tetrahydrofuran were dissolved 10 g (99 mmol) of triethylamine and 5.7 g (42 mmol) of anthranilic acid. While cooling the resulting solution with ice, 6.8 g (35 mmol) of 4-methyl-1,2,3-thiadiazole-5-carboxylic acid chloride dissolved in 10 ml of tetrahydrofuran was dropped thereto over a period of 15 minutes. After dropping it, the resulting mixture was reacted with stirring at room temperature for 15 hours. After the reaction was completed, water was added to the reaction mixture, the objective product was extracted with ethyl acetate, and the organic layer was washed successively with dilute hydrochloric acid, saturated aqueous solution of sodium hydrogen carbonate and saturated aqueous solution of sodium chloride, dried on anhydrous sodium sulfate and concentrated under reduced pressure. Purification of the residue by silica gel column chromatography using 3:1 mixture of hexane and ethyl acetate gave 1.8 g of the objective compound.

Yield: 18%.

EXAMPLE 3

Production of 2-(4-methyl-1,2,3-thiadiazol-5-yl)-4H-4-thioxo-3,1-benzothiazine (Compound No. a240)

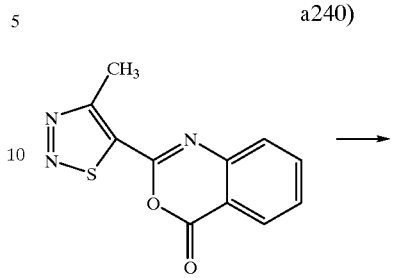

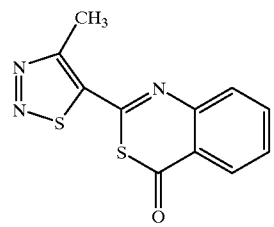

In 15 ml of toluene were suspended 1 g (4 mmol) of 2-(4-methyl-1,2,3-thiadiazol-5-yl)-4H-4-oxo-3,1-benzoxazine and 5 g of Lauesson's reagent, and the resulting mixture was reacted for 10 hours with heating under reflux. After the reaction was completed, the reaction mixture was filtered together with ether to remove precipitates, and the filtrate was concentrated under reduced pressure. Purification of the residue by silica gel column chromatography using 4:1 mixture of hexane and ethyl acetate gave 0.16 g (yield 14%) of the objective compound.

EXAMPLE 4

Production of 4-methyl-N-(4-methylphenyl)-N-morpholinothio-1,2,3-thiadiazole-5-carboxamide (Compound No. b183)

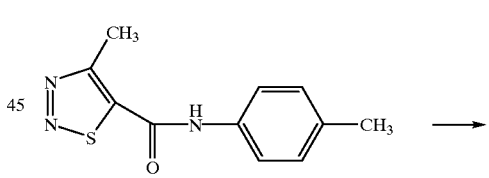

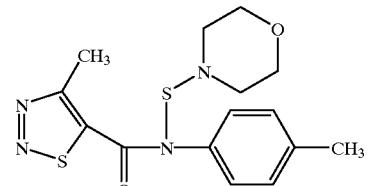

To 10 ml of methylene chloride were added 0.50 g (2.1 mmol) of 4-methyl-N-(4-methylphenyl)-1,2,3-thiadiazole-5-carboxamide and 0.50 g (3.3 mmol) of N-(chlorosulfenyl) morpholine. Then, 0.33 g (3.3 mmol) of triethylamine was slowly added thereto, and the resulting mixture was reacted with stirring for 5 hours. After the reaction was completed, the reaction mixture containing the objective product was poured into water, the objective product was extracted with ethyl acetate, the organic layer was washed with water and dried on anhydrous sodium sulfate, the solvent was distilled off under reduced pressure, and the crude crystal thus obtained was washed with ether. As a result, 0.38 g of the objective compound was obtained (Property: m.p. 60° C. (decomposed); Yield: 52%).

EXAMPLE 5

Production of 4,4'-dimethyl-N,N'-bis(4-methylphenyl)-thio-N,N'-bis(1,2,3-thiadiazole-5-carboxamide) (Compound No. b184)

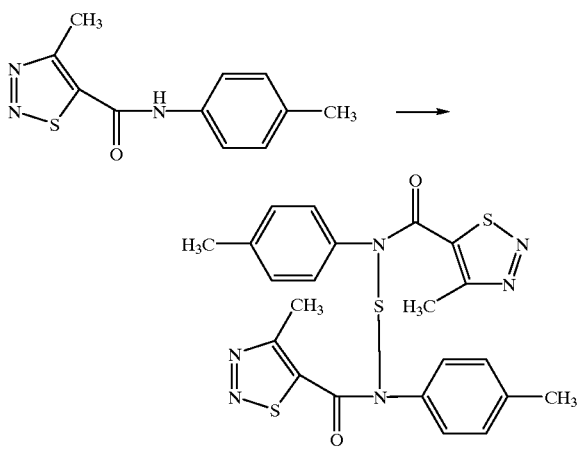

To 10 ml of methylene chloride were added 0.50 g (2.1 mmol) of 4-methyl-N-(4-methylphenyl)-1,2,3-thiadiazole-5-carboxamide and 0.14 g (1.0 mmol) of sulfur monochloride. Then, 0.22 g (2.1 mmol) of triethylamine was slowly added thereto, and the resulting mixture was reacted with stirring for 5 hours. After the reaction was completed, the reaction mixture containing the objective product was poured into water, the objective product was extracted with ethyl acetate, the organic layer was washed with water and dried on anhydrous sodium sulfate, the solvent was distilled off under reduced pressure, and the crude crystal thus obtained was washed with ether. Thus, 0.10 g of the objective compound was obtained (Property: m.p. 86° C. (decomposed): Yield: 20%).

EXAMPLE 6

Production of 4-methyl-N-methylsulfonyl-1,2,3-thiadiazole-5-carboxamide (Compound No. b408)

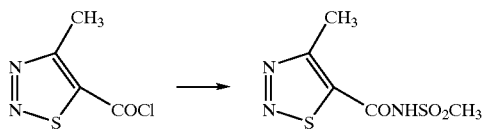

In 30 ml of tetrahydrofuran was dissolved 0.29 g (3.1 mmol) of methanesulfonamide, to which was then added 0.5 ml of triethylamine. Then, 0.50 g (3.1 mmol) of 1,2,3-thiadiazole-5-carbonyl chloride was dropwise added thereto, and the resulting mixture was reacted at room temperature for 4 hours.

After the reaction was completed, the reaction mixture containing the objective product was poured into water, the objective product was extracted with ethyl acetate, the organic layer was washed with water and dried on anhydrous sodium sulfate, the solvent was distilled off under reduced pressure, and the crude crystal thus obtained was washed with ether. Thus, 0.39 g of the objective compound was obtained. (Property: m.p. 187° C.; Yield: 57%)

EXAMPLE 7

Production of N-(4-chlorophenylsulfonyl)-4-methyl-1,2,3-thiadiazole-5-carboxamide (Compound No. b435)

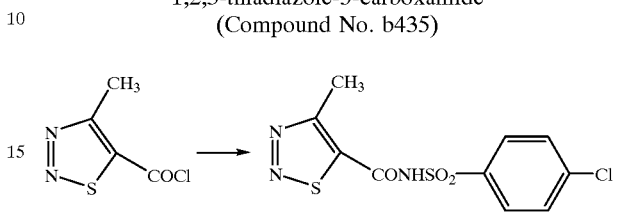

In 30 ml of tetrahydrofuran was dissolved 0.59 g (3.1 mmol) of p-chlorobenzenesulfonamide, to which was added 0.5 ml of triethylamine. Then, 0.50 g (3.1 mmol) of 1,2,3-thiadiazole-5-carbonyl chloride was dropwise added thereto, and reacted at room temperature for 4 hours.

After the reaction was completed, 100 ml of 5% aqueous hydrochloric acid was added to the reaction mixture containing the objective product, the objective product was extracted with ethyl acetate, the organic layer was washed with water and dried on anhydrous sodium sulfate, the solvent was distilled off under reduced pressure, and the crude crystal thus obtained was washed with ether. Thus, 0.14 g of the objective compound was obtained. (Property: m.p. 165° C.; Yield: 14%)

Next, typical formulation examples and test examples of the present invention are presented below.

In the formulation examples, "parts" means parts by weight.

FORMULATION EXAMPLE 1

| | |
|---|---|
| Each compound listed in Table 1 or 2 | 50 parts |
| Xylene | 40 parts |
| Mixture of polyoxyethylene nonylphenyl ether and calcium alkylbenzenesulfonate | 10 parts |

An emulsifiable concentrate was prepared by mixing the above ingredients uniformly to effect dissolution.

FORMULATION EXAMPLE 2

| | |
|---|---|
| Each compound listed in Table 1 or 2 | 3 parts |
| Clay powder | 82 parts |
| Diatomaceous earth powder | 15 parts |

A dust was prepared by mixing uniformly and grinding the above ingredients.

FORMULATION EXAMPLE 3

| Each compound listed in Table 1 or 2 | 5 parts |
|---|---|
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

FORMULATION EXAMPLE 4

| Each compound listed in Table 1 or 2 | 20 parts |
|---|---|
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

TEST EXAMPLE 1

Rice Blast-controlling Test by Submerged Application

Rice plants at the 5 to 6 leaf stage cultivated in a 1/10000-are pot were subjected to submerged application of a chemical containing each compound listed in Table 1 or 2 as an active ingredient, in a dosage of 200 g/10 a in terms of active ingredient. After standing in a greenhouse for 1 week, the plants were inoculated with a suspension of spores of blast fungus (*Pyricularia oryzae*) by spraying.

After the inoculation, the plants were allowed to stand in a moist chamber for 1 day and then in a greenhouse for 6 days to cause the disease sufficiently. Then, lesions in each leaf were counted and then compared with those on the untreated plot, and the controlling degree was calculated, whereby the effect was judged according to the following criterion.

| Effect | Controlling degree (%) |
|---|---|
| A | 100–95 |
| B | 94–85 |
| C | 84–60 |
| D | 59–0 |

As a result of the above test, the compounds listed in Table 1 and Table 2 were found to have a marked blast-controlling activity. Of these compounds, the following compounds were rated C or higher: a27, a33, a55, a107, a223, a231, a233, b183 and b184. In particular, the following were rated A: a27, a33, a55, a107, a233, b183 and b184.

What is claimed is:

1. A 1,2,3-thiadiazole derivative represented by the formula (I)':

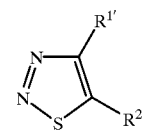
(I)' wherein $R^1$ represents hydrogen atom, $(C_1-C_6)$ alkyl group, halo $(C_1-C_6)$ alkyl group or $(C_3-C_6)$ cycloalkyl group; and $R^2$ represents a group of the formula (A):

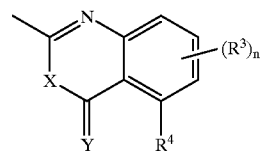
(A)

wherein $R^3$, which may be same or different, represents halogen atom, cyano group, nitro group, hydroxyl group, $(C_1-C_6)$ alkyl group, halo $(C_1-C_6)$ alkyl group, $(C_1-C_6)$ alkoxy group, halo $(C_1-C_6)$ alkoxy group or carboxyl group, n represents an integer of 0 to 3, and $R^4$ represents hydrogen atom, halogen atom, cyano group, nitro group, hydroxyl group, $(C_1-C_6)$ alkyl group, halo $(C_1-C_6)$ alkyl group, $(C_1-C_6)$ alkoxy group, halo $(C_1-C_6)$ alkoxy group or carboxyl group, further, $R^3$ or $R^3$ and $R^4$ may be taken conjointly with a carbon atom of the adjacent phenyl group to form a $(C_5-C_6)$ alkenylene ring, and X and Y may be same or different and represent oxygen atom or sulfur atom; provided that when $R^1$ is hydrogen atom, methyl group or trifluoromethyl group and n is 0, then $R^4$ is not hydrogen atom, halogen atom, nitro group, $(C_1-C_4)$ alkyl group, halo $(C_1-C_4)$ alkyl group, halo $(C_1-C_4)$ alkoxy group or cyano group.

2. A 1,2,3-thiadiazole derivative according to claim 1, wherein said 1,2,3-thiadiazole derivative is represented by the formula (I)':

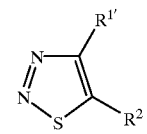
(I)' wherein $R^1$ represents hydrogen atom, $(C_1-C_6)$ alkyl group, halo $(C_1-C_6)$ alkyl group or $(C_3-C6)$ cycloalkyl group; and $R^2$ represents a group of the formula (A):

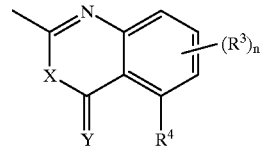
(A)

wherein $R^3$, which may be same or different, represents halogen atom, hydroxyl group, $(C_1-C_6)$ alkyl group, $(C_1-C_6)$ alkoxy group, nitro group or carboxyl group, n represents an integer of 0 to 3, $R^4$ represents halogen atom, hydroxyl group, $(C_1-C_6)$ alkyl group, $(C_1-C_6)$ alkoxy group, nitro group or carboxyl group, and X and Y may be same or different and represent oxygen atom or sulfur atom; provided that when $R^1$ is hydrogen atom, methyl group or trifluoromethyl group and n is 0, then $R^4$ is not hydrogen atom, halogen atom, nitro group, or $(C_1-C_4)$ alkyl group.

3. A 1,2,3-thiadiazole compound according to claim 1, wherein $R^1$ represents $(C_2-C_6)$ alkyl group or cyclo $(C_3-C_6)$ alkyl group, $R^2$ represents formula (A) in which $R^3$ may be same or different and represents halogen atom or $(C_1-C_6)$ alkyl group, n represents an integer of 0 to 1, $R^4$ represents hydrogen atom, halogen atom or $(C_1-C_6)$ alkyl group, and X and Y represent oxygen atoms.

4. A composition for plant disease control comprising, as an active ingredient thereof, the 1,2,3-thiadiazole compound according to claim 1, wherein, in the formula (I), $R^1$ represents hydrogen atom, $(C_1-C_6)$ alkyl group, halo $(C_1-C_6)$ alkyl group or $(C_3-C_6)$ cycloalkyl group; and $R^2$ represents a group of the formula (A):

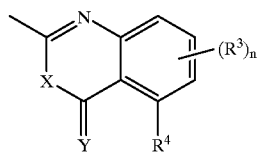
(A)

wherein $R^3$, which may be same or different, represents halogen atom, cyano group, nitro group, hydroxyl group, $(C_1-C_6)$ alkyl group, halo $(C_1-C_6)$ alkyl group, $(C_1-C_6)$ alkoxy group, halo $(C_1-C_6)$ alkoxy group or carboxyl group, n represents an integer of 0 to 3, and $R^4$ represents hydrogen atom, halogen atom, cyano group, nitro group, hydroxyl group, $(C_1-C_6)$ alkyl group, halo $(C_1-C_6)$ alkyl group, $(C_1-C_6)$ alkoxy group, halo $(C_1-C_6)$ alkoxy group or carboxyl group, further, $R^3$ or $R^3$ and $R^4$ may be taken conjointly with a carbon atom of the adjacent phenyl group to form a $(C_5-C_6)$ alkenylene ring, and X and Y may be same or different and represent oxygen atom or sulfur atom and an inert carrier.

5. A method for controlling a plant disease caused by a pathogenic organism selected from the group consisting of fungi, bacteria and viruses, comprising the steps of treating a plant to be protected with an effective quantity of the plant disease controller composition claimed in claim 4.

* * * * *